(12) United States Patent
Mates et al.

(10) Patent No.: US 8,993,572 B2
(45) Date of Patent: Mar. 31, 2015

(54) PYRIDO[3',4':4,5]PYRROLO[1,2,3-DE]QUINOXALINES DERIVATIVES AND [1,4]OXAZINO[2,3,4-HI]PYRIDO[4,3-B]INDOLE DERIVATIVES

(75) Inventors: Sharon Mates, New York, NY (US); Robert Davis, New York, NY (US); Lawrence P. Wennogle, New York, NY (US); Peng Li, New York, NY (US); John Charles Tomesch, New York, NY (US); Qiang Zhang, New York, NY (US)

(73) Assignee: Intra-Cellular Therapies, Inc., New York, NY (US)

( * ) Notice: Subject to any disclaimer, the term of this patent is extended or adjusted under 35 U.S.C. 154(b) by 0 days.

(21) Appl. No.: 13/642,652

(22) PCT Filed: Apr. 22, 2011

(86) PCT No.: PCT/US2011/000719
§ 371 (c)(1),
(2), (4) Date: Jan. 2, 2013

(87) PCT Pub. No.: WO2011/133224
PCT Pub. Date: Oct. 27, 2011

(65) Prior Publication Data
US 2013/0202692 A1   Aug. 8, 2013

Related U.S. Application Data

(60) Provisional application No. 61/327,049, filed on Apr. 22, 2010, provisional application No. 61/367,609, filed on Jul. 26, 2010.

(51) Int. Cl.
*A61K 31/4985* (2006.01)
*C07D 241/36* (2006.01)
*C07D 471/16* (2006.01)
*C07D 471/04* (2006.01)
*A61K 31/44* (2006.01)

(52) U.S. Cl.
CPC ............ *C07D 471/16* (2013.01); *C07D 471/04* (2013.01); *A61K 31/44* (2013.01)
USPC .......................................... 514/250; 544/350

(58) Field of Classification Search
CPC ........................... A61K 31/4985; C07D 241/36
USPC .......................................... 514/250; 544/350
See application file for complete search history.

(56) References Cited

U.S. PATENT DOCUMENTS

| | | | |
|---|---|---|---|
| 4,389,330 A | 6/1983 | Tice et al. | |
| 4,530,840 A | 7/1985 | Tice et al. | |
| 5,538,739 A | 7/1996 | Bodmer et al. | |
| 6,548,493 B1 | 4/2003 | Robichaud et al. | |
| 6,552,017 B1 | 4/2003 | Robichaud et al. | |
| 6,713,471 B1 | 3/2004 | Robichaud et al. | |
| 7,081,455 B2 | 7/2006 | Robichaud et al. | |
| 7,183,282 B2 | 2/2007 | Robichaud et al. | |
| RE39,679 E | 6/2007 | Robichaud et al. | |
| RE39,680 E | 6/2007 | Robichaud et al. | |
| 7,238,690 B2 | 7/2007 | Robichaud et al. | |
| 8,309,722 B2 | 11/2012 | Tomesch et al. | |
| 8,648,077 B2 | 2/2014 | Tomesch et al. | |
| 2004/0092534 A1 | 5/2004 | Yam et al. | |
| 2004/0180875 A1 | 9/2004 | Lee et al. | |
| 2004/0220178 A1 | 11/2004 | Robichaud et al. | |
| 2008/0069885 A1 | 3/2008 | Mesens et al. | |
| 2008/0280941 A1 | 11/2008 | Lourtie | |
| 2009/0202631 A1 | 8/2009 | Yam et al. | |

FOREIGN PATENT DOCUMENTS

| | | |
|---|---|---|
| EP | 0 058 481 B2 | 8/1982 |
| GB | 2145422 A | 3/1985 |

(Continued)

OTHER PUBLICATIONS

Khorana, et al., "Gamma-Carbolines: Binding at 5-HT5A Receptors", Bioorganic & Medicinal Chemistry, (2003), vol. 11, Issue 5, 6, pp. 717-722, p. 718 Table 1.
March, *Advanced Organic Chemistry; Reactions, Mechanisms and Structures*, Fourth Edition, pp. 910-911 (1992).
U.S. Appl. No. 61/975,702, filed Apr. 4, 2014, Vanover et al.
U.S. Appl. No. 61/925,607, filed Jan. 9, 2014, Vanover et al.
U.S. Appl. No. 61/911,416, filed Dec. 3, 2013, Vanover et al.
U.S. Appl. No. 62/015,120, filed Jun. 20, 2014, Mates et al.
U.S. Appl. No. 61/975,502, filed Apr. 4, 2014, Mates et al.
U.S. Appl. No. 62/009,849, filed Jun. 9, 2014, Davis et al.

(Continued)

*Primary Examiner* — Douglas M Willis
(74) *Attorney, Agent, or Firm* — Hoxie & Associates, LLC

(57) ABSTRACT

The invention relates to particular substituted heterocycle fused gamma-carbolines of formula I:

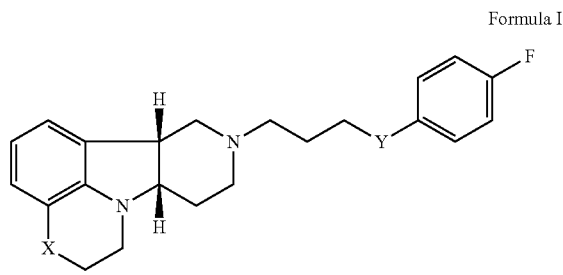

Formula I as described herein, their prodrugs, in free, solid, pharmaceutically acceptable salt and/or substantially pure form as described herein, pharmaceutical compositions thereof, and methods of use in the treatment of diseases involving 5-HT$_{2A}$ receptor, serotonin transporter (SERT) and/or pathways involving dopamine D2 receptor signaling systems.

19 Claims, 2 Drawing Sheets

(56) References Cited

FOREIGN PATENT DOCUMENTS

| | | |
|---|---|---|
| WO | WO 00/35419 A2 | 6/2000 |
| WO | WO 00/77002 A1 | 12/2000 |
| WO | WO 2008/112280 A1 | 9/2008 |
| WO | WO 2009/114181 A2 | 9/2009 |
| WO | WO 2009/145900 | 12/2009 |
| WO | WO 2013/155504 | 10/2013 |
| WO | WO 2013/155505 | 10/2013 |
| WO | WO 2013/155506 | 10/2013 |
| WO | PCT/US2014/029914 | 3/2014 |

OTHER PUBLICATIONS

U.S. Appl. No. 61/975,610, filed Apr. 4, 2014, Mates et al.

Pond, S.M. et al. "Stereospecific reduction of haloperidol in human tissues". *Biochemical Pharmacology*, vol. 44 (5), p. 867-871 (1992).

Data are presented as mean ± SEM.

* and ** indicate statistically significant difference between drug treatments and vehicle treatment at 5 and 1% levels, respectively.

# and # # indicates statistically significant difference between Haloperidol and drug treatments at 5 and 1% levels, respectively.

PYRIDO[3',4':4,5]PYRROLO[1,2,3-DE]QUINOXALINES DERIVATIVES AND [1,4]OXAZINO[2,3,4-HI]PYRIDO[4,3-B]INDOLE DERIVATIVES

CROSS REFERENCE TO RELATED APPLICATIONS

This application is a national phase application filed under 35 U.S.C. §371 of International Application No. PCT/US2011/000719, filed Apr. 22, 2011, which claims the benefit of U.S. Provisional Application 61/327,049, filed Apr. 22, 2010 and U.S. Provisional Application 61/367,609, filed Jul. 26, 2010, the contents of each of which are incorporated by reference in their entirety.

FIELD OF THE INVENTION

The invention relates to particular substituted heterocycle fused gamma-carbolines, their prodrugs, in free, solid, pharmaceutically acceptable salt and/or substantially pure form as described herein, pharmaceutical compositions thereof, and methods of use in the treatment of diseases involving 5-$HT_{2A}$ receptor, serotonin transporter (SERT) and/or pathways involving dopamine $D_2$ receptor signaling systems, e.g., diseases or disorders such as anxiety, psychosis, schizophrenia, sleep disorders, sexual disorders, migraine, conditions associated with cephalic pain, social phobias, gastrointestinal disorders such as dysfunction of the gastrointestinal tract motility and obesity; depression and mood disorders associated with psychosis or Parkinson's disease; psychosis such as schizophrenia associated with depression; bipolar disorder; and other psychiatric and neurological conditions, as well as to combinations with other agents.

BACKGROUND OF THE INVENTION

Substituted heterocycle fused gamma-carbolines are known to be agonists or antagonists of 5-HT2 receptors, particularly 5-$HT_{2A}$ and 5-$HT_{2C}$ receptors, in treating central nervous system disorders. These compounds have been disclosed in U.S. Pat. Nos. 6,548,493; 7,238,690; 6,552,017; 6,713,471; 7,183,282; U.S. RE39680, and U.S. RE39679, as novel compounds useful for the treatment of disorders associated with 5-$HT_{2A}$ receptor modulation such as obesity, anxiety, depression, psychosis, schizophrenia, sleep disorders, sexual disorders migraine, conditions associated with cephalic pain, social phobias, gastrointestinal disorders such as dysfunction of the gastrointestinal tract motility, and obesity. PCT/US08/03340 (WO 2008/112280) and U.S. application Ser. No. 10/786,935 also disclose methods of making substituted heterocycle fused gamma-carbolines and uses of these gamma-carbolines as serotonin agonists and antagonists useful for the control and prevention of central nervous system disorders such as addictive behavior and sleep disorders.

In addition, WO/2009/145900 discloses use of particular substituted heterocycle fused gamma-carbolines for the treatment of a combination of psychosis and depressive disorders as well as sleep, depressive and/or mood disorders in patients with psychosis or Parkinson's disease. In addition to disorders associated with psychosis and/or depression, this patent application discloses and claims use of these compounds at a low dose to selectively antagonize 5-$HT_{2A}$ receptors without affecting or minimally affecting dopamine $D_2$ receptors, thereby useful for the treatment of sleep disorders without the side effects of the dopamine $D_2$ pathways or side effects of other pathways (e.g., $GABA_A$ receptors) associated with convention sedative-hypnotic agents (e.g., benzodiazepines) including but not limited to the development of drug dependency, muscle hypotonia, weakness, headache, blurred vision, vertigo, nausea, vomiting, epigastric distress, diarrhea, joint pains, and chest pains. WO 2009/114181 also discloses of methods of preparing toluenesulfonic acid addition salt crystals of these substituted heterocycle fused gamma-carbolines.

SUMMARY OF THE INVENTION

While substituted heterocycle fused gamma-carbolines and their uses are known, we have surprisingly found that particular substituted heterocycle fused gamma-carbolines ("Compounds of Formula I" as hereinafter described), while less active in ex vivo assays than a first drug ("Compounds of Formula Q", as hereinafter described), are inter-converted to and from the first drug within the plasma and the brain. Because these Compounds of Formula I convert in vivo to and from the Compounds of Formula Q, they can be considered as prodrugs for Compounds of Formula Q, as well as metabolites of Compounds of Formula Q, and can serve as a reservoir for the Compounds of Formula Q, extending its duration of action. The duration of action and metabolism of these Compounds of Formula I can be modified further through attachment of physiologically hydrolysable and acceptable moieties and/or the use of extended release formulations. Our inventors thus have further provide prodrugs of particular substituted heterocycle fused gamma-carbolines that have altered pharmacokinetic profile, e.g., altered mechanisms and/or rate of absorption and distribution, and therefore may be useful for an improved formulation and/or for controlling the duration of the effect of the drug in the body (e.g., for sustained- or controlled release). The invention therefore provides compounds and their prodrugs, their pharmaceutical composition, for use as set forth herein.

It is further discovered that the Compounds of Formula I moreover have interesting neurotransmitter receptor binding activity different from Compounds of Formula Q. In particular, Compounds of Formula I as hereinafter described wherein Y is —CH(OH)— are shown to have high selectivity for the serotonin transporter (SERT) relative to Compounds of Formula Q, and can thus enhance the effect of Compounds of Formula Q on SERT. This unique profile offers particular utility in treatment of SERT-mediated diseases, such as depression, anxiety, and psychosis with depression or anxiety.

Without intending to be bound by theory, it is believed that while Compounds of Formula I where Y is —C(H)(OH)—, convert to Compounds of Formula Q in vivo, administration of Compounds of Formula I could have certain advantages over administration of Compounds of Formula Q directly, in that the Compounds of Formula I would provide a longer duration of action, due to their metabolic stability and continuous conversion to Compounds of Formula Q, and moreover would enhance SERT inhibitory activity as compared to activity at other receptors, due to their relatively high activity at the SERT receptor.

The invention relates to a compound of formula I:

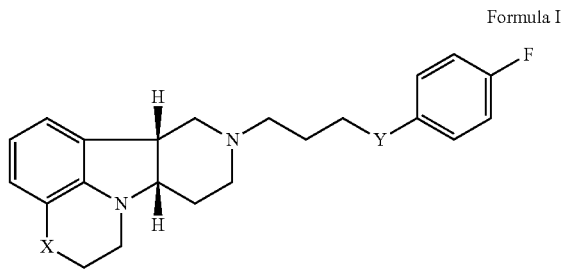

Formula I wherein:
X is —N(H)— or —N(CH₃) and Y is —C(H)(OH)—;
X is —N(H) when Y is —O—; or
X is —O— and Y is —C(H)(OH)—;
in free or salt form.

In the first aspect, the invention provides the Compound of Formula I, in free or salt form as described in the following formulae:

1.1 the Compound of Formula I, provided that the compound is not produced in a mammal by metabolism of the compound of Formula Q:

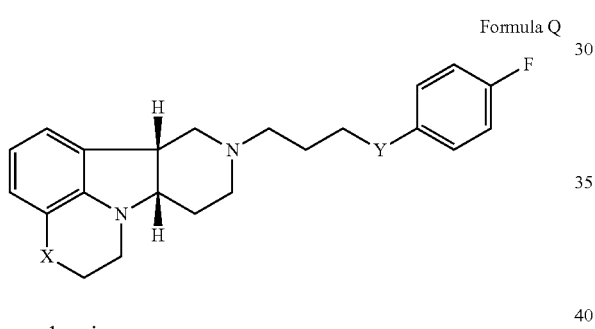

Formula Q wherein
X is —N(H)— or —N(CH₃)— and/or Y is —C(=O);
X is —N(CH₃)— and Y is —O—; or
X is —O— and Y is —C(=O)—;

1.2 the Compound of Formula I or 1.1, wherein said compound is in solid form;
1.3 the Compound of Formula I, 1.1 or 1.2, wherein said compound is in salt form;
1.4 the Compound of Formula I or any of formulae 1.1-1.3, wherein said compound is in pharmaceutically acceptable salt form;
1.5 formula 1.4, wherein the pharmaceutically acceptable salt is selected from a group consisting of hydrochloric, hydrobromic, sulfuric, sulfamic, phosphoric, nitric, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like;
1.6 formula 1.5, wherein the salt is a fumeric acid addition salt;
1.7 formula 1.5, wherein the salt is a phosphoric acid addition salt;
1.8 formula 1.5, wherein the salt is a toluenesulfonic acid addition salt;

1.9 the Compound of Formula I or any of formulae 1.1-1.8, wherein the Compound is:

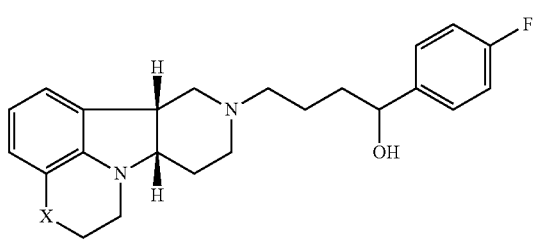

1.10 the Compound of Formula I or any of 1.1-1.9, wherein the Compound is:

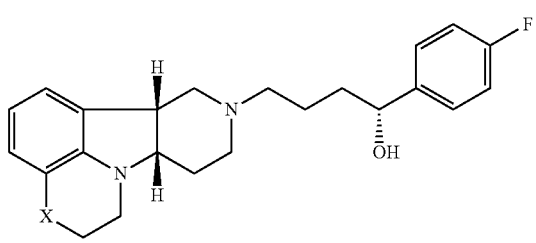

1.11 the Compound of Formula I or any of 1.1-1.9, wherein the Compound is:

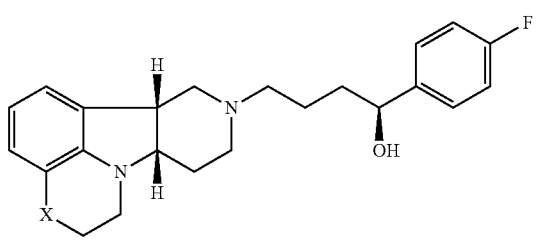

1.12 the Compound of Formula I or any of 1.1-1.11, wherein X is —N(CH₃);
1.13 the Compound of Formula I or any of 1.1-1.11, wherein X is —N(H)—;
1.14 the Compound of Formula I or any of 1.1-1.12, wherein the Compound is:

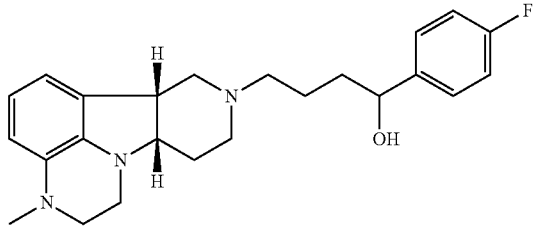 [SMILES: CN1CCN2c3c(cccc31)[C@@H]1CN(CCCC(O)c3ccc(F)cc3)CC[C@@H]12]

1.15 the Compound of Formula I or any of 1.1-1.11, wherein X is —O—;
1.16 the Compound of Formula I or any of 1.9-1.15, wherein the Compound is in substantially pure diastereomeric form (i.e., substantially free from other diastereomers);
1.17 the Compound of Formula I or any of 1.9-1.16, wherein the Compound has a diasteromeric excess of greater than 70%, preferably greater than 80%, more preferably greater than 90% and most preferably greater than 95%;

1.18 the Compound of Formula I or any of formulae 1.1-1.8, wherein the Compound is

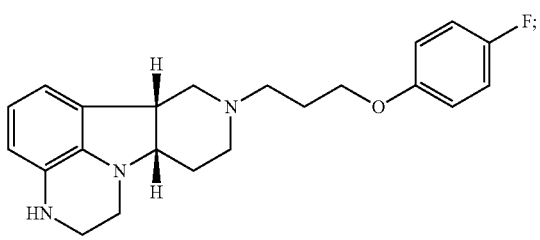 [SMILES: Fc1ccc(OCCCN2CC[C@H]3[C@@H](C2)c2cccc4c2N3CCN4)cc1]

1.19 the Compound of Formula I or any of formulae 1.1-1.18, wherein said compound is substantially free of the compound of Formula Q as hereinbefore defined;

1.20 formula 1.19, wherein the Compound of Formula I is:

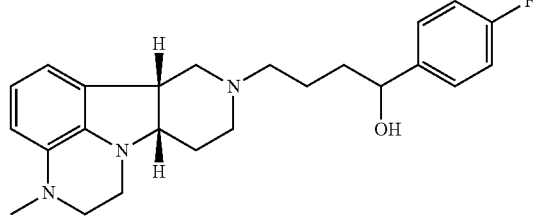

substantially free of a Compound of Formula Q wherein Y is —C(=O) and/or X is —N(CH$_3$)—;

1.21 formula 1.19, wherein the Compound of Formula I is:

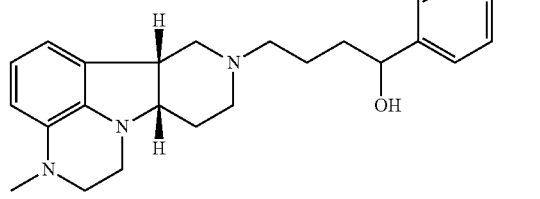

substantially free of a Compound of Formula Q wherein Y is —C(=O) and/or X is —N(CH$_3$)— or —N(H)—;

1.22 any of formulae 1.19-1.21, wherein the Compound of Formula I is greater than 70%, preferably greater than 80%, more preferably greater than 90%, still more preferably greater than 95%, still more preferably greater than 98%, still more preferably greater than 99% free of the Compound of Formula Q as described in any of formulae 1.1-1.21, in free or salt form In the second aspect, the invention provides a compound of Formula II-A:

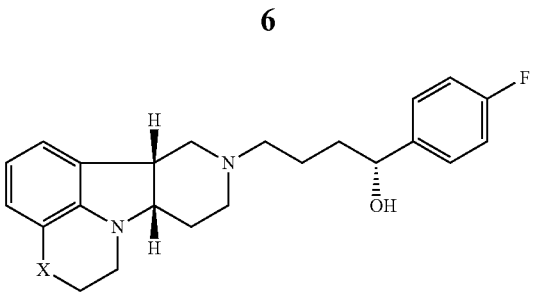

wherein X is —N(CH$_3$)—, —N(H)— or —O—, in free or salt form. In a further embodiment of the second aspect, the invention provides a compound of Formula II-A wherein X is —N(CH$_3$)—. In still another further embodiment of the second aspect, the invention provides a compound of Formula II-A wherein X is —N(H)—.

In the third aspect, the invention provides a compound of Formula II-B:

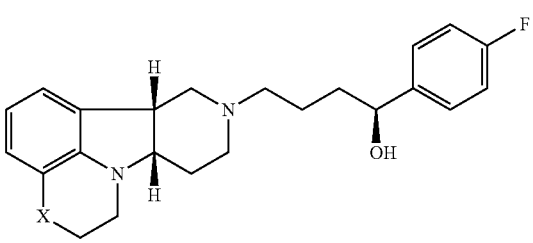

wherein X is —N(CH$_3$)—, —N(H)— or —O—, in free or salt form. In a further embodiment of the third aspect, the invention provides a compound of Formula II-B, wherein X is —N(CH$_3$)—. In still another further embodiment of the third aspect, the invention provides a compound of Formula II-B, wherein X is —N(H)—.

In the fourth aspect, the invention provides a Compound of Formula III:

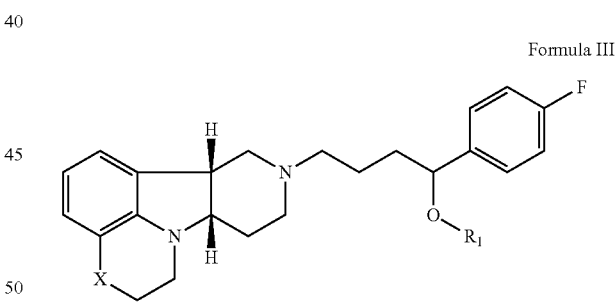

Formula III wherein:
X is —N(CH$_3$)—, —N(H)— or —O—; and
R$_1$ is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated and optionally substituted with one or more hydroxy or C$_{1-22}$alkoxy (e.g., ethoxy) groups, for example R$_1$ is —C(O)—C$_6$alkyl, —C(O)—C$_7$alkyl, —C(O)—C$_9$alkyl, —C(O)—C$_{11}$alkyl, —C(O)—C$_{13}$alkyl or —C(O)—C$_{15}$alkyl and such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand), in free or salt form.

In a further embodiment of the fourth aspect, the invention provides a Compound of Formula III, in free or salt form as described in the following formulae:

4.1. the Compound of Formula III, wherein the salt is selected from a group consisting of hydrochloric, hydrobromic, sulfuric, sulfamic, phosphoric, nitric, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like;

4.2. the Compound of Formula III or formula 4.1, wherein the salt is fumeric acid addition salt;

4.3. the Compound of Formula III or formula 4.1, wherein the salt is phosphoric acid addition salt;

4.4. the Compound of Formula III or formula 4.1, wherein the salt is a toluenesulfonic acid addition salt;

4.5. the Compound of Formula III or any of formulae 4.1-4.4, wherein the Compound is:

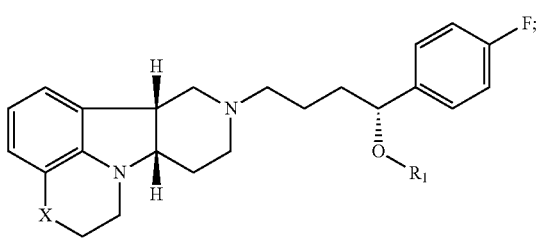

4.6. the Compound of Formula III or any of formulae 4.1-4.4, wherein the Compound is:

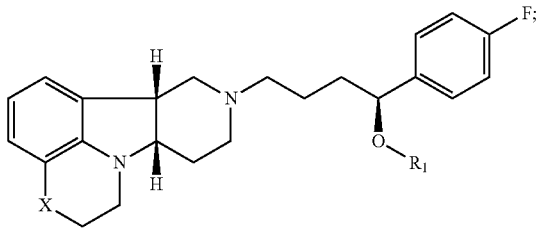

4.7. the Compound of Formula III or any of formulae 4.1-4.6, wherein the Compound is in substantially pure diastereomeric form (i.e., substantially free from other diastereomers);

4.8. the Compound of Formula III or any of 4.1-4.7, wherein the Compound has a diasteromeric excess of greater than 70%, preferably greater than 80%, more preferably greater than 90% and most preferably greater than 95%;

4.9. the Compound of Formula III or any of formulae 4.1-4.8, wherein X is —N(CH$_3$);

4.10. the Compound of Formula III or any of formulae 4.1-4.8, wherein X is —N(H)—;

4.11. the Compound of Formula III or any of formulae 4.1-4.10, wherein R$_1$ is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated and optionally substituted with one or more hydroxy or C$_{1-22}$alkoxy (e.g., ethoxy) groups, for example R$_1$ is —C(O)—C$_6$alkyl, —C(O)—C$_7$alkyl, —C(O)—C$_9$alkyl, —C(O)—C$_{1-21}$alkyl, —C(O)—C$_{13}$alkyl or —C(O)—C$_{15}$alkyl and such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand);

4.12. the Compound of Formula III or any of formulae 4.1-4.11, wherein R$_1$ is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated;

4.13. the Compound of Formula III or any of formulae 4.1-4.11, wherein R$_1$ is —C(O)—C$_{1-21}$alkyl (e.g., —C(O)—C$_{1-5}$alkyl, —C(O)—C$_{6-15}$alkyl or —C(O)—C$_{16-21}$alkyl);

4.14. the Compound of Formula III or any of formulae 4.1-4.11, wherein R$_1$ is selected from —C(O)—C$_6$alkyl, —C(O)—C$_7$alkyl, —C(O)—C$_9$alkyl, —C(O)—C$_{11}$alkyl, —C(O)—C$_{13}$alkyl and —C(O)—C$_{15}$alkyl;

4.15. the Compound of Formula III or any of formulae 4.1-4.11, wherein R$_1$ is —C(O)—C$_6$alkyl;

4.16. the Compound of Formula III or any of formulae 4.1-4.11, wherein R$_1$ is —C(O)—C$_7$alkyl;

4.17. the Compound of Formula III or any of formulae 4.1-4.11, wherein R$_1$ is —C(O)—C$_9$alkyl;

4.18. the Compound of Formula III or any of formulae 4.1-4.11, wherein R$_1$ is —C(O)—C$_{11}$alkyl;

4.19. the Compound of Formula III or any of formulae 4.1-4.11, wherein R$_1$ is —C(O)—C$_{13}$alkyl;

4.20. the Compound of Formula III or any of formulae 4.1-4.11, wherein R$_1$ is —C(O)—C$_{15}$alkyl;

4.21. the Compound of Formula III or any of formulae 4.1-4.11, wherein R$_1$ is —C(O)—C$_{17}$alkyl;

4.22. the Compound of Formula III or any of formulae 4.1-4.11, wherein R$_1$ is —C(O)—C$_{21}$ alkyl;

4.23. the Compound of Formula III or any of formulae 4.1-4.8 or 4.11-1.14, wherein X is —O—;

4.24. the Compound of Formula III or any of formulae 4.1-4.23, wherein said compound is substantially free of the compound of Formula Q as in any of formulae 1.1-1.21;

4.25. formula 4.24, wherein the Compound of Formula III is:

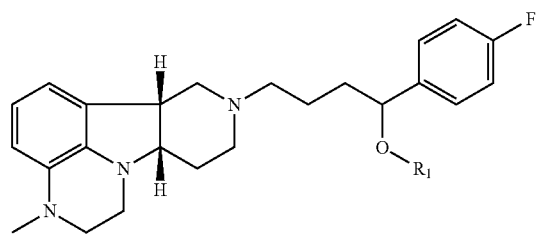

substantially free of a Compound of Formula Q wherein Y is —C(═O) and/or X is —N(CH$_3$)—;

4.26. formula 4.24, wherein the Compound of Formula III is:

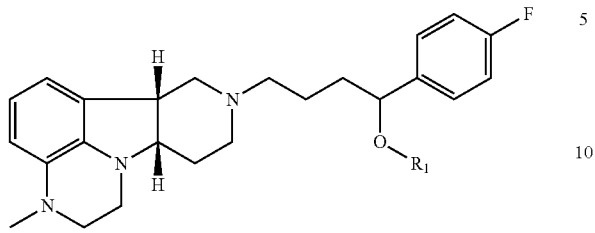

substantially free of a Compound of Formula Q wherein Y is —C(=O) and/or X is —N(CH₃)— or —N(H)—;

4.27. any of formulae 4.24-4.26, wherein the Compound of Formula III is greater than 70%, preferably greater than 80%, more preferably greater than 90%, still more preferably greater than 95%, still more preferably greater than 98%, still more preferably greater than 99% free of the Compound of Formula Q as described in any of formulae 1.1-1.21;

in free or salt form.

In another further embodiment of the fourth aspect, the invention provides a Compound of Formula III, in free or salt form as described in any one of the following formulae:

4.28. the Compound of Formula III, or any of 4.1-4.13 or 4.23-4.27, wherein R₁ is —C(O)—C₃alkyl;

4.29. the Compound of Formula III, or any of 4.1-4.13 or 4.23-4.27, wherein R₁ is —C(O)—C₉alkyl;

4.30. the Compound of Formula III, wherein said compound is selected from any one of the following:

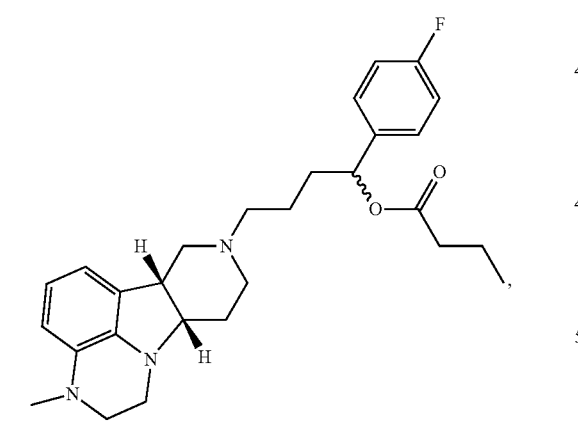

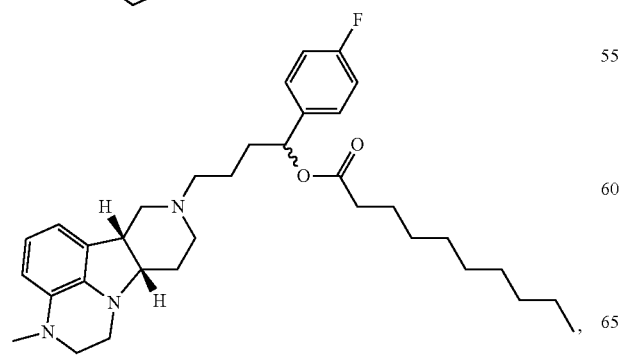

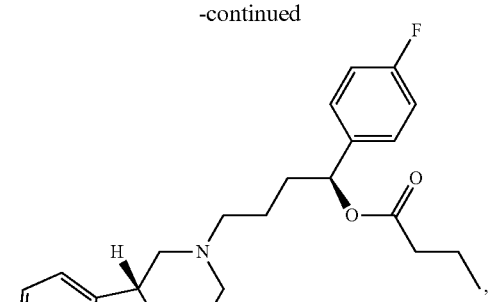

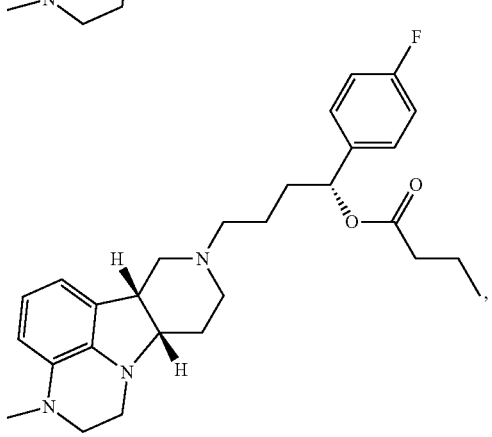

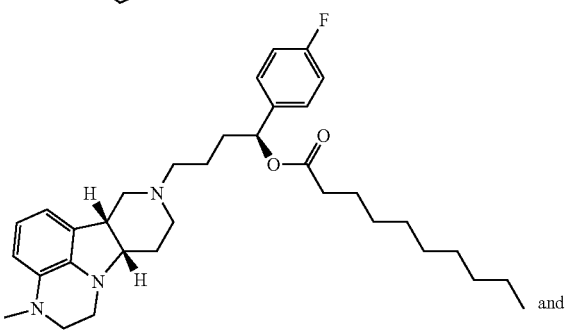

and

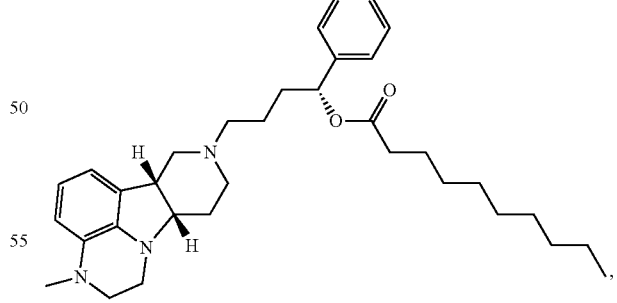

in free or salt form.

In the fifth aspect, the invention provides a pharmaceutical composition as described in the following formulae:

5.1 A Pharmaceutical Composition comprising a Compound of Formula I or any of formulae 1.1-1.22 as hereinbefore described, in free or pharmaceutically acceptable salt form, in admixture with a pharmaceutically acceptable diluent or carrier (Pharmaceutical Composition 5.1);

5.2 A Pharmaceutical Composition comprising a Compound of Formula II-A as hereinbefore described, in free or pharmaceutically acceptable salt form, in admixture with a pharmaceutically acceptable diluent or carrier (Pharmaceutical Composition 5.2);

5.3 A Pharmaceutical Composition comprising a Compound of Formula II-B as hereinbefore described, in free or pharmaceutically acceptable salt form, in admixture with a pharmaceutically acceptable diluent or carrier (Pharmaceutical Composition 5.3); or 5.4 A Pharmaceutical Composition comprising a Compound of Formula III or any of formulae 4.1-4.27 as hereinbefore described, in free or pharmaceutically acceptable salt form, in admixture with a pharmaceutically acceptable diluent or carrier (Pharmaceutical Composition 5.4);

5.4P A Pharmaceutical Composition comprising a Compound of Formula III or any of formulae 4.28-4.30 as hereinbefore described, in free or pharmaceutically acceptable salt form, in admixture with a pharmaceutically acceptable diluent or carrier (Pharmaceutical Composition 5.4P).

In a preferred embodiment, the Pharmaceutical Composition of the Invention comprises a Compound of Formula I wherein X is —N(CH$_3$)— and Y is —C(H)(OH)—, in free or pharmaceutically acceptable salt form, in admixture with a pharmaceutically acceptable diluent or carrier. In another embodiment, the Pharmaceutical Composition of the Invention comprises a Compound of Formula 1.14, in free or pharmaceutically acceptable salt form, in admixture with a pharmaceutically acceptable diluent or carrier. In still another embodiment, the Pharmaceutical Composition of the Invention comprises a Compound of Formula 4.26, in free or pharmaceutically acceptable salt form, in admixture with a pharmaceutically acceptable diluent or carrier. In yet another embodiment, the Pharmaceutical Composition of the Invention comprises a Compound of Formula 4.20, in free or pharmaceutically acceptable salt form, in admixture with a pharmaceutically acceptable diluent or carrier.

In a further embodiment of the fifth aspect, the Pharmaceutical Composition of the Invention is for a sustained or delayed release, e.g., depot, formulation. In one embodiment, the depot formulation is the Pharmaceutical Composition 5.4 (Depot Composition 5.5). In a further embodiment, the Depot Composition 5.5 comprises a Compound of Formula III, wherein R$_1$ is a —C(O)—C$_{6-15}$alkyl, in free or pharmaceutically acceptable salt form (Depot Composition 5.6). For example, depot formulation is a pharmaceutical composition comprising:

5.7 1-(4-Fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-enanthrate (i.e., Compound of Formula III, wherein X is —N(CH$_3$)— and R$_1$ is —C(O)—C$_6$alkyl); (Depot Composition 5.7);

5.8 1-(4-Fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-decanoate, (i.e., Compound of Formula III, wherein X is —N(CH$_3$)— and R$_1$ is —C(O)—C$_{19}$alkyl) (Depot Composition 5.8); or 5.9 1-(4-Fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-palmitate (i.e., Compound of Formula III, wherein X is —N(CH$_3$)— and R$_1$ is —C(O)—C$_{15}$alkyl); (Depot Composition 5.9), in free or pharmaceutically acceptable salt form, in admixture with a pharmaceutically acceptable diluent or carrier.

In another embodiment of the fifth aspect, the depot formulation is the Pharmaceutical Composition 5.4P (Depot Composition 5.10). For example, depot formulation is a pharmaceutical composition comprising:

5.11 1-(4-Fluoro-phenyl)-4-46bR,10aS)-3-methyl-2,3,6b,9,10,10a-hexahydro-1H,7H-pyrido[3',4':4,5]pyrrolo[1,2,3-de]quinoxalin-8-yl)-butan-1-butanoate (i.e., Compound of Formula III, wherein X is —N(CH$_3$)— and R$_1$ is —C(O)—C$_3$alkyl); (Depot Composition 5.11), in free or pharmaceutically acceptable salt form, in admixture with a pharmaceutically acceptable diluent or carrier.

In the sixth aspect, the invention provides a composition comprising a Compound of the Invention as described in the following formulae:

6.1. of Formula I or any of formulae 1.1-1.22, in free or (pharmaceutically acceptable) salt form (Composition 6.1);

6.2. of Formula II-A, in free or (pharmaceutically acceptable) salt form (Composition 6.2);

6.3. of Formula II-B, in free or (pharmaceutically acceptable) salt form (Composition 6.3); or 6.4. of Formula III or any of formulae 4.1-4.27 as hereinbefore described, in free or (pharmaceutically acceptable) salt form (Composition 6.4);

6.5. of Formula III or any of formulae 4.28-4.30 as hereinbefore described, in free or (pharmaceutically acceptable) salt form (Composition 6.5), in a polymeric matrix. In one embodiment, the Compounds of the Invention is dispersed or dissolved within the polymeric matrix. In a further embodiment, the polymeric matrix comprises standard polymers used in depot formulations such as polymers selected from apolyester of a hydroxyfatty acid and derivatives thereof, or a polymer of an alkyl alpha-cyanoacrylate, a polyalkylene oxalate, a polyortho ester, a polycarbonate, a polyortho-carbonate, a polyamino acid, a hyaluronic acid ester, and mixtures thereof. In a further embodiment, the polymer is selected from a group consisting of polylactide, poly d,l-lactide, poly glycolide, PLGA 50:50, PLGA 85:15 and PLGA 90:10 polymer. In another embodiment, the polymer is selected form poly(glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. In a preferred embodiment, the polymeric matrix comprises poly(d,l-lactide-co-glycolide). For example, the Composition of any of formulae 6.1-6.4 wherein the Compound of the Invention is the Compound of Formula I, wherein X is —N(CH$_3$)— and Y is —C(H)(OH)—, in free or salt form. In another example, the Composition of formula 6.5, wherein the Compound of the Invention is the Compound of Formula III, wherein X is —N(CH$_3$)— and R$_1$ is —C(O)—C$_3$alkyl or —C(O)—C$_9$alkyl, in free or salt form. In another embodiment, the Compound of the Invention is the Compound of formula 1.14, 4.26 or 4.20, in free or salt form and the polymeric matrix comprises a poly(d,l-lactide-co-cylcolide). Any of Compositions of formulae 6.1-6.4 as hereinbefore described may be a pharmaceutical composition wherein said composition is in admixture with a pharmaceutically acceptable diluent or carrier (Pharmaceutical Composition 6.1-6.4). Similarly, any of Compositions of formulae 6.5 as hereinbefore described may be a pharmaceutical composition wherein said composition is in admixture with a pharmaceutically acceptable diluent or carrier (Pharmaceutical Composition 6.5).

The (Pharmaceutical) Compositions of any of formulae 6.1-6.4 are particularly useful for sustained or delayed release, wherein the Compound of the Invention is released upon degradation of the polymeric matrix. These Compositions may be formulated for controlled- and/or sustained-release of the Compounds of the Invention (e.g., as a depot composition) over a period of up to 180 days, e.g., from about 14 to about 30 to about 180 days. For example, the polymeric matrix may degrade and release the Compounds of the Invention over a period of about 30, about 60 or about 90 days. In another example, the polymeric matrix may degrade and release the Compounds of the Invention over a period of about 120, or about 180 days.

In still another further embodiment, the Pharmaceutical Compositions of the Invention, particularly the depot composition of the Invention (e.g., Depot Composition of any of formulae 5.5-5.9 or (Pharmaceutical) Composition of any of formulae 6.1-6.4 or 6.5) is formulated for administration by injection.

In the seventh aspect, the invention provides the Compound of the Invention as hereinbefore described, e.g.,
- a Compound of Formula I or any of formulae 1.1-1.22 as hereinbefore described, in free or pharmaceutically acceptable salt form;
- a Compound of Formula II-A as hereinbefore described, in free or pharmaceutically acceptable salt form;
- a Compound of Formula II-B as hereinbefore described, in free or pharmaceutically acceptable salt form; or
- a Compound of Formula III or any of formulae 4.1-4.30 as hereinbefore described, in free or pharmaceutically acceptable salt form;

in an osmotic controlled release oral delivery system (OROS), which is described in WO 2000/35419 and EP 1 539 115 (U.S. Pub. No. 2009/0202631), the contents of each of which applications are incorporated by reference in their entirety. Therefore in one embodiment of the seventh aspect, the invention provides a pharmaceutical composition or device comprising (a) a gelatin capsule containing a Compound of the Invention in free or pharmaceutically acceptable salt form or a Pharmaceutical Composition of the Invention, as hereinbefore described; (b) a multilayer wall superposed on the gelatin capsule comprising, in outword order from the capsule: (i) a barrier layer, (ii) an expandable layer, and (iii) a semipermeable layer; and (c) and orifice formed or formable through the wall. (Composition P.1)

In another embodiment of the seventh aspect, the invention provides a composition comprising a gelatin capsule containing a liquid, the Compound of the Invention in free or pharmaceutically acceptable salt form or a Pharmaceutical Composition of the Invention, e.g., any of Pharmaceutical Composition 6.1-6.5, the gelatin capsule being surrounded by a composite wall comprising a barrier layer contacting the external surface of the gelatin capsule, an expandable layer contacting the barrier layer, a semi-permeable layer encompassing the expandable layer, and an exit orifice formed or formable in the wall. (Composition P.2)

In still another embodiment of the seventh aspect, the invention provides a composition comprising a gelatin capsule containing a liquid, the Compound of the Invention in free or pharmaceutically acceptable salt form or a Pharmaceutical Composition of the Invention, e.g., any of Pharmaceutical Composition 6.1-6.5, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall, wherein the barrier layer forms a seal between the expandable layer and the environment at the exit orifice. (Composition P.3)

In still another embodiment of the seventh aspect, the invention provides a composition comprising a gelatin capsule containing a liquid, the Compound of the Invention in free or pharmaceutically acceptable salt form or a Pharmaceutical Composition of the Invention, e.g., any of Pharmaceutical Composition 6.1-6.5, the gelatin capsule being surrounded by a barrier layer contacting the external surface of the gelatin capsule, an expandable layer contacting a portion of the barrier layer, a semi-permeable layer encompassing at least the expandable layer, and an exit orifice formed or formable in the dosage form extending from the external surface of the gelatin capsule to the environment of use. (Composition P.4). The expandable layer may be formed in one or more discrete sections, such as for example, two sections located on opposing sides or ends of the gelatin capsule.

In a particular embodiment of the seventh aspect, the Compound of the Invention in the Osmotic-controlled Release Oral delivery System (i.e., in Composition P.1-P.4) is in a liquid formulation, which formulation may be neat, liquid active agent, liquid active agent in a solution, suspension, emulsion or self-emulsifying composition or the like.

Further information on Osmotic-controlled Release Oral delivery System composition including characteristics of the gelatin capsule, barrier layer, an expandable layer, a semi-permeable layer; and orifice may be found in WO 2000/35419, the contents of which are incorporated by reference in their entirety.

Other Osmotic-controlled Release Oral delivery System for the Compound or the Pharmaceutical Composition of the Invention may be found in EP 1 539 115 (U.S. Pub. No. 2009/0202631), the contents of which are incorporated by reference in their entirety. Therefore, in another embodiment of the seventh aspect, the invention provides a composition or device comprising (a) two or more layers, said two or more layers comprising a first layer and a second layer, said first layer comprises the Compound of the Invention, in free or pharmaceutically acceptable salt form, or a Pharmaceutical Composition as herein before described said second layer comprises a polymer; (b) an outer wall surrounding said two or more layers; and (c) an orifice in said outer wall. (Composition P.5)

Composition P.5 preferably utilizes a semi-permeable membrane surrounding a three-layer-core: in these embodiments the first layer is referred to as a first drug layer and contains low amounts of drug (e.g., the Compound of the Invention) and an osmotic agent such as salt, the middle layer referred to as the second drug layer contains higher amounts of drug, excipients and no salt; and the third layer referred to as the push layer contains osmotic agents and no drug. At least one orifice is drilled through the membrane on the first drug layer end of the capsule-shaped tablet. (Composition P.6)

Composition P.5 or P.6 may comprise a membrane defining a compartment, the membrane surrounding an inner protective subcoat, at least one exit orifice formed or formable therein and at least a portion of the membrane being semi-permeable; an expandable layer located within the compartment remote from the exit orifice and in fluid communication with the semi-permeable portion of the membrane; a first drug layer located adjacent the exit orifice; and a second drug layer located within the compartment between the first drug layer and the expandable layer, the drug layers comprising the Compound of the Invention in free or pharmaceutically acceptable salt thereof. Depending upon the relative viscosity of the first drug layer and second drug layer, different release profiles are obtained. It is imperative to identify the optimum viscosity for each layer. In the present invention, viscosity is modulated by addition of salt, sodium chloride. The delivery profile from the core is dependent on the weight, formulation and thickness of each of the drug layers. (Composition P.7)

In a particular embodiment, the invention provides Composition P.7 wherein the first drug layer comprising salt and the second drug layer containing no salt. Composition P.5-P.7 may optionally comprise a flow-promoting layer between the membrane and the drug layers.

Compositions P.1-P.7 will generally be referred to as Osmotic-controlled Release Oral delivery System Composition.

In the eighth aspect, the invention provides a method (Method I) for the treatment or prophylaxis of a central nervous system disorder, comprising administering to a patient in need thereof:

7.1 a Compound of Formula I or any of formulae 1.1-1.22, in free or pharmaceutically acceptable salt form;
7.2 Compound of Formula II-A, in free or pharmaceutically acceptable salt form;
7.3 Compound of Formula II-B, in free or pharmaceutically acceptable salt form;
7.4 Compound of Formula III or any of formulae 4.1-4.27 as hereinbefore described, in free or pharmaceutically acceptable salt form;
7.5 a Pharmaceutical Composition as described in formula 5.1;
7.6 a Pharmaceutical Composition as described in formula 5.2;
7.7 a Pharmaceutical Composition as described in formula 5.3;
7.8 a Pharmaceutical Composition as described in formula 5.4;
7.9 Depot Composition of any of formulae 5.5-5.9; or
7.10 (Pharmaceutical) Composition of any of formulae 6.1-6.4 as hereinbefore described;

In a further embodiment of the eighth aspect, the invention provides Method I or any of Formulae 7.1-7.10, wherein the method is further as described in the following formulae:

7.11 Method I or any of Formulae 7.1-7.10, wherein the central nervous system disorder is a disorder selected from a group consisting of obesity, anxiety, depression (for example refractory depression and MDD), psychosis, schizophrenia, sleep disorders (particularly sleep disorders associated with schizophrenia and other psychiatric and neurological diseases), sexual disorders, migraine, conditions associated with cephalic pain, social phobias, agitation in dementia (e.g., agitation in Alzheimer's disease), agitation in autism and related autistic disorders, and gastrointestinal disorders such as dysfunction of the gastrointestinal tract motility;
7.12 Method I or any of Formulae 7.1-7.10, wherein the central nervous system disorder is a disorder involving serotonin 5-HT$_2$A, dopamine D2 receptor system and/or serotonin reuptake transporter (SERT) pathways as similarly described in WO/2009/145900, the contents of which are herein incorporated by reference in their entirety;
7.13 Method I or any of Formulae 7.1-7.12, wherein the central nervous system disorder is a disorder selected from the following: (i) psychosis, e.g., schizophrenia, in a patient suffering from depression; (2) depression in a patient suffering from psychosis, e.g., schizophrenia; (3) mood disorders associated with psychosis, e.g., schizophrenia or Parkinson's disease; and (4) sleep disorders associated with psychosis, e.g., schizophrenia or Parkinson's disease;
7.14 Method I or any of Formulae 7.1-7.13, wherein the central nervous system disorder is psychosis, e.g., schizophrenia and said patient is a patient suffering from depression;
7.15 Method I or any of Formulae 7.1-7.14, wherein said patient is unable to tolerate the side effects of convention antipsychotic drugs, e.g., chlorpromazine, haloperidol droperidol, fluphenazine, loxapine, mesoridazine molidone, perphenazine, pimozide, prochlorperazine promazine, thioridazine, thiothixene, trifluoperazine, clozapine, aripiparazole, olanzapine, quetiapine, risperidone and ziprasidone;
7.16 Method I or any of Formulae 7.1-7.15, wherein said patient is unable to tolerate the side effects of convention antipsychotic drugs, e.g., haloperidol, aripiparazole, clozapine, olanzapine, quetiapine, risperidone, and zipasidone;
7.17 Method I or any of Formulae 7.1-7.16, wherein said disorder is depression and said patient is a patient suffering from psychosis, e.g., schizophrenia, or Parkinson's disease;
7.18 Method I or any of Formulae 7.1-7.13, wherein said disorder is sleep disorder and said patient is suffering from depression;
7.19 Method I or any of 7.1-7.13, wherein said one or more disorders is sleep disorder and said patient is suffering from psychosis, e.g., schizophrenia;
7.20 Method I or any of 7.1-7.13, wherein said one or more disorders is sleep disorder and said patient is suffering from Parkinson's disease;
7.21 Method I or any of 7.1-7.13, wherein said one or more disorders is sleep disorder and said patient is suffering from depression and psychosis, e.g., schizophrenia, or Parkinson's disease.
7.22 Any of the foregoing methods, wherein the effective amount is 1 mg-1000 mg, preferably 2.5 mg-50 mg;
7.23 Any of the foregoing methods, wherein the effective amount is 1 mg-100 mg per day, preferably 2.5 mg-50 mg per day;
7.24 Any of the foregoing methods wherein a condition to be treated is dyskinesia, e.g. in a patient receiving dopaminergic medications, e.g., medications selected from levodopa and levodopa adjuncts (carbidopa, COMT inhibitors, MAO-B inhibitors), dopamine agonists, and anticholinergics, e.g., levodopa;
7.25 Any of the foregoing methods wherein the patient suffers from Parkinson's disease.

In a particular embodiment of the eighth aspect, the invention provides a method (Method Ip) for the treatment or prophylaxis of a central nervous system disorder, comprising administering to a patient in need thereof:

7.4P a compound of Formula III or any of formulae 4.28-4.30 as hereinbefore described, in free or (pharmaceutically acceptable) salt form;
7.8P a Pharmaceutical Composition as described in 5.4P;
7.9P Depot Composition of any of formulae 5.10-5.11;
7.10P (Pharmaceutical) Composition of formula 6.5 as hereinbefore described;
7.11P Osmotic-controlled Release Oral delivery System Composition as hereinbefore described.

In a further embodiment of the eighth aspect, the invention provides Method Ip, wherein the method is further described in any one of formulae 7.11-7.25.

In a preferred embodiment of the eighth aspect, the invention provides Method I or any of 7.1-7.25, wherein the compound is a Compound of Formula I, wherein X is —N(CH$_3$)— and Y is —C(H)(OH)—, in free or pharmaceutitically acceptable salt form. In another preferred embodiment, the invention provides Method I or any of 7.1-7.25, wherein the compound is a Compound of Formula 1.14, 4.26 or 4.20, in free or pharmaceutically acceptable salt form. In still another preferred embodiment, the invention provides the method as hereinbefore described wherein the disorder is schizophrenia or sleep disorder.

In still another preferred embodiment of the eighth aspect, the invention provides Method I or any of 7.1-7.25, wherein the Depot Composition of the Invention (Depot Composition of any of formulae 5.5-5.9; or (Pharmaceutical) Composition of any of formulae 6.1-6.4) is administered for controlled- and/or sustained-release of the Compounds of the Invention over a period of from about 14 days, about 30 to about 180 days, preferably over the period of about 30, about 60 or about 90 days. Controlled- and/or sustained-release is particularly useful for circumventing premature discontinuation of therapy, particularly for antipsychotic drug therapy where non-compliance or non-adherence to medication regimes is a common occurrence.

In still another preferred embodiment of the eighth aspect, the invention provides Method $I_P$ as hereinbefore described, wherein the Depot Composition of the Invention is administered for controlled- and/or sustained-release of the Compounds of the Invention over a period of time.

In the ninth aspect, the invention provides a method (Method II) for the prophylaxis or treatment one or more sleep disorders comprising administering to a patient in need thereof a compound as described in the following formulae:
- 8.1 a Compound of Formula I or any of formulae 1.1-1.22, in free or pharmaceutically acceptable salt form;
- 8.2 Compound of Formula II-A, in free or pharmaceutically acceptable salt form;
- 8.3 Compound of Formula II-B, in free or pharmaceutically acceptable salt form;
- 8.4 Compound of Formula III or any of formulae 4.1-4.27 as hereinbefore described, in free or pharmaceutically acceptable salt form;
- 8.5 a Pharmaceutical Composition as described in formula 5.1;
- 8.6 a Pharmaceutical Composition as described in formula 5.2;
- 8.7 a Pharmaceutical Composition as described in formula 5.3;
- 8.8 a Pharmaceutical Composition as described in formula 5.4;
- 8.9 Depot Composition of any of formulae 5.5-5.9; or
- 8.10 (Pharmaceutical) Composition of any of formulae 6.1-6.4 as hereinbefore described In a further embodiment of the ninth aspect, the invention provides Method II,
- 8.1-8.10, wherein the sleep disorder includes sleep maintenance insomnia, frequent awakenings, and waking up feeling unrefreshed;
- 8.11 Any of the foregoing methods, wherein the sleep disorder is sleep maintenance insomnia;
- 8.12 Any of the foregoing methods, wherein the effective amount is 1 mg-5 mg, preferably 2.5-5 mg, per day;
- 8.13 Any of the foregoing methods, wherein the effective amount is 2.5 mg or 5 mg, per day;
- 8.14 Any of the foregoing methods wherein the sleep disorder is in a patient suffering from or at risk of dyskinesia, e.g., a patient receiving dopaminergic medications, e.g., selected from levodopa and levodopa adjuncts (carbidopa, COMT inhibitors, MAO-B inhibitors), dopamine agonists, and anticholinergics, e.g., receiving levodopa;
- 8.15 Any of the foregoing methods wherein the patient suffers from Parkinson's disease.

In another embodiment of the ninth aspect, the invention provides a method (Method $II_P$) for the prophylaxis or treatment one or more sleep disorders comprising administering to a patient in need thereof a compound as described in the following formulae:
- 8.4P Formula III or any of formulae 4.28-4.30 as hereinbefore described, in free or (pharmaceutically acceptable) salt form;
- 8.8P a Pharmaceutical Composition as described in 5.4P;
- 8.9P Depot Composition of any of formulae 5.10-5.11;
- 8.10P (Pharmaceutical) Composition of formula 6.5 as hereinbefore described;
- 8.11P Osmotic-controlled Release Oral delivery System Composition as hereinbefore described.

In a further embodiment of the ninth aspect, the invention provides Method $II_P$, or any of 8.4P, 8.8P-8.11P, wherein the sleep disorder includes sleep maintenance insomnia, frequent awakenings, and waking up feeling unrefreshed. In still another embodiment of the ninth aspect, Method $II_P$ is as described in any of formulae 8.11-8.15.

The Compounds of Invention, upon conversion to the Compound of Formula Q as hereinbefore described, provides effective treatment of 5-HT2A, SERT and/or $D_2$ receptor related disorders without or with minimal extrapyramidal side effects as similarly disclosed and claimed in WO 2009/145900, the contents of which are incorporated by reference in their entirety. Therefore, the Compounds of the Invention, the Pharmaceutical Compositions of the Invention or the Depot Compositions of the Invention may be used in combination with a second therapeutic agent, particularly at lower dosages than when the individual agents are used as a monotherapy so as to enhance the therapeutic activities of the combined agents without causing the undesirable side effects commonly occur in conventional monotherapy. Therefore, the Compounds of the Invention may be simultaneously, sequentially, or contemporaneously administered with other anti-depressant, anti-psychotic, other hypnotic agents, and/or agents use to treat Parkinson's disease or mood disorders. In another example, side effects may be reduced or minimized by administering a Compound of the Invention in combination with one or more second therapeutic agents in free or salt form, wherein the dosages of (i) the second therapeutic agent(s) or (ii) both Compound of the Invention and the second therapeutic agents, are lower than if the agents/compounds are administered as a monotherapy. In a particular embodiment, the Compounds of the Invention are useful to treat dyskinesia in a patient receiving dopaminergic medications, e.g., selected from levodopa and levodopa adjuncts (carbidopa, COMT inhibitors, MAO-B inhibitors), dopamine agonists, and anticholinergics, e.g., such as are used in the treatment of Parkinson's disease.

Therefore, in the tenth aspect, the current invention provides Method I, e.g., or any of formulae 7.1-7.25, or Method II or any of 8.1-8.15, further comprises one or more therapeutic agents selected from compounds that modulate GABA activity (e.g., enhances the activity and facilitates GABA transmission), a GABA-B agonist, a 5-HT modulator (e.g., a 5-HT1a agonist, a 5-HT$_{2A}$ antagonist, a 5-HT2a inverse agonist, etc.), a melatonin agonist, an ion channel modulator (e.g., blocker), a serotonin-2 antagonist/reuptake inhibitor (SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, and an antipsychotic agent, e.g., an atypical antipsychotic agent, in free or pharmaceutically acceptable salt form (Method I-A and II-A respectively).

In a further embodiment of the tenth aspect, the invention provides Method I-A or II-A as follows, further comprising one or more therapeutic agents.

9.1 Method I-A or II-A, wherein the therapeutic agent(s) is compounds that modulate GABA activity (e.g., enhances the activity and facilitates GABA transmission);

9.2 Method I-A or II-A or 9.1, wherein the GABA compound is selected from a group consisting of one or more of doxepin, alprazolam, bromazepam, clobazam, clonazepam, clorazepate, diazepam, flunitrazepam, fiurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals) and estazolam;

9.3 Method I-A or II-A, wherein the therapeutic agent is an additional 5HT2a antagonist;

9.4 Method I-A or II-A or 9.3, wherein said additional 5HT2a antagonist is selected from one or more of ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, Calif.), and AVE8488 (Sanofi-Aventis, France);

9.5 Method I-A or II-A, wherein the therapeutic agent is a melatonin agonist;

9.6 Method I-A or II-A or 9.5, wherein the melatonin agonist is selected from a group consisting of one or more of melatonin, ramelteon (ROZEREM®, Takeda Pharmaceuticals, Japan), VEC-162 (Vanda Pharmaceuticals, Rockville, Md.), PD-6735 (Phase II Discovery) and agomelatine;

9.7 Method I-A or II-A, wherein the therapeutic agent is an ion channel blocker;

9.8 Method I-A or II-A or 9.7, wherein said ion channel blocker is one or more of lamotrigine, gabapentin and pregabalin.

9.9 Method I-A or II-A, wherein the therapeutic agent is an orexin receptor antagonist;

9.10 Method I-A or II-A or 9.9, wherein the orexin receptor antagonist is selected from a group consisting of orexin, a 1,3-biarylurea, SB-334867-a (GlaxoSmithKline, UK), GW649868 (GlaxoSmithKline) and a benzamide derivative;

9.11 Method I-A or II-A, wherein the therapeutic agent is the serotonin-2 antagonist/reuptake inhibitor (SARI);

9.12 Method I-A or II-A or 9.11, wherein the serotonin-2 antagonist/reuptake inhibitor (SARI) is selected from a group consisting of one or more Org 50081 (Organon-Netherlands), ritanserin, nefazodone, serzone and trazodone;

9.13 Method I-A or II-A, wherein the therapeutic agent is the 5HTIa agonist;

9.14 Method I-A or II-A or 9.13, wherein the 5HTIa agonist is selected from a group consisting of one or more of repinotan, sarizotan, eptapirone, buspirone and MN-305 (MediciNova, San Diego, Calif.);

9.15 Method I-A or II-A, wherein the therapeutic agent is the neurokinin-1 drug;

9.16 Method I-A or II-A or 9.15, wherein the neurokinin-1 drug is Casopitant (GlaxoSmithKline);

9.17 Method I-A or II-A, wherein the therapeutic agent is an antipsychotic agent;

9.18 Method I-A or II-A or 9.17, wherein the antipsychotic agent is selected from a group consisting of chlorpromazine, haloperidol, droperidol, fluphenazine, loxapine, mesoridazine molidone, perphenazine, pimozide, prochlorperazine promazine, thioridazine, thiothixene, trifluoperazine, clozapine, aripiparazole, olanzapine, quetiapine, risperidone, ziprasidone and paliperidone;

9.19 Method I-A or II-A, wherein the therapeutic agent is an anti-depressant;

9.20 Method I-A or II-A or 9.19, wherein the anti-depressant is selected from amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenlzine sulfate, protiptyline, sertraline, tranylcypromine, trazodone, trimipramine, and velafaxine;

9.21 Method I-A or II-A, 9.17 or 9.18, wherein the antipsychotic agent is an atypical antipsychotic agent;

9.22 Method I-A or II-A, or any of 9.17-9.21, wherein the atypical antipsychotic agent is selected from a group consisting of clozapine, aripiparazole, olanzapine, quetiapine, risperidone, ziprasidone, and paliperidone;

9.23 Method I-A or II-A, wherein the therapeutic agent is selected from any of methods 9.1-9.22, e.g., selected from a group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals), estazolam, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, Calif.), AVE8488 (Sanofi-Aventis, France), repinotan, sarizotan, eptapirone, buspirone, MN-305 (MediciNova, San Diego, Calif.), melatonin, ramelteon (ROZEREM®, Takeda Pharmaceuticals, Japan), VEC-162 (Vanda Pharmaceuticals, Rockville, Md.), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon-Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenlzine sulfate, protiptyline, sertraline, tranylcypromine, trazodone, trimipramine, velafaxine, chlorpromazine, haloperidol, droperidol, fluphenazine, loxapine, mesoridazine molidone, perphenazine, pimozide, prochlorperazine promazine, thioridazine, thiothixene, trifluoperazine, clozapine, aripiparazole, olanzapine, quetiapine, risperidone, ziprasidone and paliperidone;

9.24 Method I-A or II-A wherein the therapeutic agent is an H3 agonist;

9.25 Method I-A or II-A, wherein the therapeutic agent is an H3 antagonist;

9.26 Method I-A or II-A, wherein the therapeutic agent is a noradrenergic agonist or antagonist;

9.27 Method I-A or II-A, wherein the therapeutic agent is a galanin agonist;

9.28 Method I-A or II-A, wherein the therapeutic agent is a CRH antagonist;

9.29 Method I-A or II-A, wherein the therapeutic agent is a human growth hormone;

9.30 Method I-A or II-A, wherein the therapeutic agent is a growth hormone agonist;

9.31 Method I-A or II-A, wherein the therapeutic agent is estrogen;

9.32 Method I-A or II-A, wherein the therapeutic agent is an estrogen agonist;

9.33 Method I-A or II-A, wherein the therapeutic agent is a neurokinin-1 drug;

9.34 Method I-A or II-A, wherein a therapeutic agent is combined with compounds of Formula (I) and the therapeutic agent is an anti-Parkinson agent such as L-dopa, co-careldopa, duodopa, stalova, Symmetrel, benzotropine, biperiden, bromocryiptine, entacapone, pergolide, pramipexole, procyclidine, ropinirole, selegiline and tolcapone;

9.35 Method I-A or II-A, wherein compounds of Formula (I) may be used to treat sleep disorders, depression, pyschosis, or any combinations thereof, in patients suffering from the listed diseases and/or Parkinson's disease;

9.36 Method I-A or II-A, wherein the disorder is selected from at least one or more of psychosis, e.g., schizophrenia, depression, mood disorders, sleep disorders (e.g., sleep maintenance and/or sleep onset) or any combination of disorders thereof;

9.37 Any of the foregoing methods wherein the disorder is sleep disorder;

9.38 Any of the foregoing methods, wherein the disorder is sleep disorder associated with psychosis, e.g., schizophrenia or Parkinson's disease; in free or pharmaceutically acceptable salt form.

In another embodiment of the tenth aspect, the current invention provides Method $I_P$ or Method $II_P$ as hereinbefore described, further comprises one or more therapeutic agents selected from compounds that modulate GABA activity (e.g., enhances the activity and facilitates GABA transmission), a GABA-B agonist, a 5-HT modulator (e.g., a 5-HTIa agonist, a 5-HT$_{2A}$ antagonist, a 5-HT2a inverse agonist, etc.), a melatonin agonist, an ion channel modulator (e.g., blocker), a serotonin-2 antagonist/reuptake inhibitor (SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, and an antipsychotic agent, e.g., an atypical antipsychotic agent, in free or pharmaceutically acceptable salt form (Method $I_P$-A and $II_P$-A respectively). In a further embodiment of this aspect, the invention provides Method $I_P$-A or $II_P$-A as similarly described in any one of formulae 9.1-9.38.

In the eleventh aspect of the invention, the combination of a Compound of the Invention and one or more second therapeutic agents as described in Methods I-A, II-A or any of 9.1-9.38, may be administered as a Pharmaceutical Composition or a depot Composition as hereinbefore described. Similarly, the combination of a Compound of the Invention and one or more second therapeutic agents as described in Methods $I_P$-A, $II_P$-A or any of 9.1-9.38, may be administered as a Pharmaceutical Composition or a depot Composition as hereinbefore described. The combination compositions can include mixtures of the combined drugs, as well as two or more separate compositions of the drugs, which individual compositions can be, for example, co-administered together to a patient.

In a particular embodiment, Methods I-A, II-A, $I_P$-A, $II_P$-A or any of 9.1-9.38 comprises administering to a patient in need thereof, a Compound of the Invention in combination with an atypical antipsychotic agent, e.g., a compound selected from clozapine, aripiparazole, olanzapine, quetiapine, risperidone, ziprasidone, or paliperidone, in free or pharmaceutically acceptable salt form, for example wherein the dosage of the atypical antipsychotic agent is reduced and/or side effects are reduced.

In another embodiment, Methods I-A, II-A, Methods $I_P$-A, $II_P$-A or any of 9.1-9.38 comprises administering to a patient in need thereof, a Compound of the Invention in combination with an anti-depressant, e.g., amitriptyline, amoxapine, bupropion, citalopram, clomipramine, desipramine, doxepin, duloxetine, escitaloprame, fluoxetine, fiuvoxamine, imipramine, isocarboxazid, maprotiline, mirtazapine, nefazodone, nortriptyline, paroxetine, phenlzine sulfate, protiptyline, sertraline, tranylcypromine, trazodone, trimipramine, or velafaxine, in free or pharmaceutically acceptable salt form. Alternatively, the anti-depressant may be used as an adjunct medication in addition to the compound of the Invention.

In still another embodiment, Methods I-A, II-A, $I_P$-A, $II_P$-A or any of 9.1-9.38 comprises administering to a patient in need thereof, a Compound of the Invention in combination with a compound that modulates GABA activity, e.g., a compound selected from doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gabaxadol, vigabatrin, tiagabine, EVT 201 (Evotec Pharmaceuticals), estazolam or any combinations thereof, in free or pharmaceutically acceptable salt form.

In another preferred embodiment, Methods I-A, II-A, $I_P$-A, $H_p$-A or any of 9.1-9.38 comprises administering to a patient in need thereof, a Compound of the Invention in combination with doxepin in free or pharmaceutically acceptable salt form. Dosages of doxepin can vary in any range known to a person of ordinary skill in the art. In one example, a 10 mg dose of doxepin may be combined with any dosage of a compound of the Invention.

In another embodiment, Methods I-A, II-A, $I_P$-A, $H_p$-A or any of 9.1-9.38 comprises administering to a patient in need thereof, a Compound of the Invention in combination (including as part of a daily dosage regimen) with an atypical stimulant, e.g., a modafinil, adrafinil, or armodafinil. A regimin incorporating a Compound of the Invention with such drugs promotes more regular sleep, and avoids side effects such as psychosis or mania associated with higher levels of such drugs, e.g., in the treatment of bipolar depression, cognition associated with schizophrenia, and excessive sleepiness and fatigue in conditions such as Parkinson's disease and cancer.

In the twelfth aspect, the invention provides use of a compound as described in the following formulae:

11.1 Compound of Formula I or any of formulae 1.1-1.22, in free or pharmaceutically acceptable salt form;

11.2 Compound of Formula II-A, in free or pharmaceutically acceptable salt form;

11.3 Compound of Formula II-B, in free or pharmaceutically acceptable salt form;

11.4 Compound of Formula III or any of formulae 4.1-4.27 as hereinbefore described, in free or pharmaceutically acceptable salt form;

11.5 a Pharmaceutical Composition as described in formula 5.1;
11.6 a Pharmaceutical Composition as described in formula 5.2;
11.7 a Pharmaceutical Composition as described in formula 5.3;
11.8 a Pharmaceutical Composition as described in formula 5.4;
11.9 Depot Composition of any of formulae 5.5-5.9; or
11.10 (Pharmaceutical) Composition of any of formulae 6.1-6.4 as hereinbefore described,
11.4P Compound of Formula III or any of formulae 4.28-4.30 as hereinbefore described, in free or (pharmaceutically acceptable) salt form;
11.8P a Pharmaceutical Composition as described in 5.4P;
11.9P Depot Composition of any of formulae 5.10-5.11;
11.10P (Pharmaceutical) Composition of formula 6.5 as hereinbefore described;
8.11P Osmotic-controlled Release Oral delivery System Composition as hereinbefore described,
(in the manufacture of a medicament) for the treatment or prophylaxis of one or more disorders as disclosed hereinbefore, e.g., in any of Method I, any of 7.1-7.25, Method II, any of 8.1-8.15, Methods I-A, II-A, any of 9.1-9.38, Method $I_P$, Method $II_P$, Methods $I_P$-A, $II_P$-A, or any methods described in the eleventh aspect of the invention.

In the thirteenth aspect, the invention provides a pharmaceutical composition as hereinbefore described, e.g., in the following formulae:
12.1 a Pharmaceutical Composition as described in formula 5.1;
12.2 a Pharmaceutical Composition as described in formula 5.2;
12.3 a Pharmaceutical Composition as described in formula 5.3;
12.4 a Pharmaceutical Composition as described in formula 5.4;
12.5 Depot Composition of any of formulae 5.5-5.9; or
12.6 (Pharmaceutical) Composition of any of formulae 6.1-6.4 as hereinbefore described,
12.8P a Pharmaceutical Composition as described in 5.4P;
12.9P Depot Composition of any of formulae 5.10-5.11;
12.10P (Pharmaceutical) Composition of formula 6.5 as hereinbefore described;
12.11P Osmotic-controlled Release Oral delivery System Composition as hereinbefore described,
for use in the treatment or prophylaxis of one or more disorders as disclosed hereinbefore, e.g., in any of Method I, any of 7.1-7.25, Method II, any of 8.1-8.15, Methods I-A, II-A, any of 9.1-9.38 Method $I_P$, Method $II_P$, Methods $I_P$-A, $II_P$-A, or any methods described in the eleventh or twelfth aspect of the invention.

DETAILED DESCRIPTION OF THE INVENTION

Figure 1:
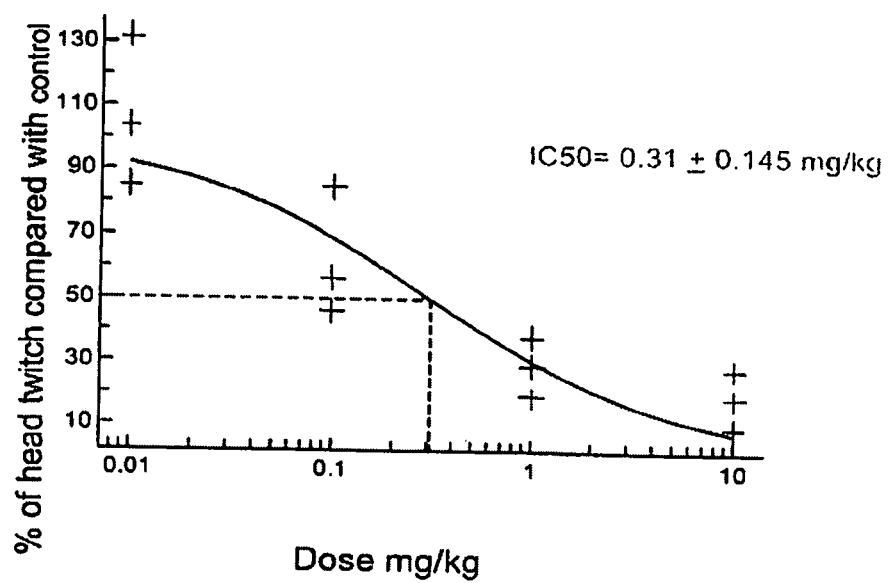
FIG. 1 illustrates the inhibition of DOI-induced head twitches in mice by the compound of Example 1 as described in Example 8.

If not otherwise specified or clear from context, the following terms as used herein have the following meetings:

a. "Alkyl" as used herein is a saturated or unsaturated hydrocarbon moiety, e.g., one to twenty-one carbon atoms in length, which may be linear or branched (e.g., n-butyl or tert-butyl), preferably linear, unless otherwise specified. For example, "$C_{1-21}$ alkyl" denotes alkyl having 1 to 21 carbon atoms. In one embodiment, alkyl is optionally substituted with one or more hydroxy or $C_{1-22}$alkoxy (e.g., ethoxy) groups. In another embodiment, alkyl contains 1 to 21 carbon atoms, preferably straight chain and optionally saturated or unsaturated, for example $R_1$ is an alkyl chain containing 1 to 21 carbon atoms, preferably 6-15 carbon atoms, 16-21 carbon atoms, e.g., so that together with the —C(O)— to which it attaches, e.g., when cleaved from the compound of Formula III, forms the residue of a natural or unnatural, saturated or unsaturated fatty acid.

Unless otherwise indicated, the Compounds of the Invention, e.g., Compounds of Formula I or any of 1.1-1.22, Formula II-A, Formula II-B, or Formula III or any of formulae 4.1-4.27 or 4.28-4.30 may exist in free or salt, e.g., as acid addition salts, form. An acid-addition salt of a compound of the invention which is sufficiently basic, for example, an acid-addition salt with, for example, an inorganic or organic acid, for example hydrochloric, hydrobromic, sulphuric, phosphoric, acid acetic, trifluoroacetic, citric, maleic acid, toluene sulfonic, propionic, succinic, glycolic, stearic, lactic, malic, tartaric, citric, ascorbic, pamoic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acid, and the like. In addition a salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)-amine. In a particular embodiment, the salt of the Compounds of the Invention is a toluenesulfonic acid addition salt. In another particular embodiment, the salt of the Compounds of the Invention is a fumeric acid addition salt. In a particular embodiment, the salt of the Compounds of the Invention is a phosphoric acid addition salt.

The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention, and are therefore also included.

The Compounds of the Invention may comprise one or more chiral carbon atoms. The compounds thus exist in individual isomeric, e.g., enantiomeric or diasteriomeric form or as mixtures of individual forms, e.g., racemic/diastereomeric mixtures. Any isomer may be present in which the asymmetric center is in the (R)-, (S)-, or (R,S)-configuration. The invention is to be understood as embracing both individual optically active isomers as well as mixtures (e.g., racemic/diasteromeric mixtures) thereof. Accordingly, the Compounds of the Invention may be a racemic mixture or it may be predominantly, e.g., in pure, or substantially pure, isomeric form, e.g., greater than 70% enantiomeric/diastereomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like).

Geometric isomers by nature of substituents about a double bond or a ring may be present in cis (Z) or trans (E) form, and both isomeric forms are encompassed within the scope of this invention.

Compounds of the Invention may in some cases also exist in prodrug form. The term "prodrug" is an art recognized term and refers to a drug precursor prior to administration, but generates or releases the active metabolite in vivo following administration, via some chemical or physiological process. In some instances, the Compound of the Invention may be a prodrug as well as a metabolite. Our inventors have surprisingly found that the Compounds of the Invention, particularly the compounds bearing the free hydroxy group, e.g., the Compound of Formula I or II, wherein X is —N(CH$_3$) and Y is —C(H)(OH)— is a relatively inactive compound (or less active than a compound wherein —C(O)—, wherein the hydroxy group on said compound is oxidized in vivo to form the active 1-(4-Fluoro-phenyl)-4-(6bR,10aS)-3-methyl-2,3, 6b,9,10,10a-hexahydro-1H,7H-pyrido[3',4':4,5]pyrrolo[1,2, 3-de]quinoxalin-8-yl)-butan-1-one (i.e., Formula Q, wherein X is —N(CH$_3$)— and Y is —C(=O)—). This active parent compound bearing the ketone group can also be metabolized back to the relatively inactive hydroxy metabolite/prodrug (e.g., Formula I wherein X is —N(CH$_3$)— and Y is —C(H)(OH)). Without intending to be bound by any particular theory, it is believed that the active Compound of Formula Q wherein —N(CH$_3$)— and Y is —C(=O) is continuously formed from the Compounds of the Invention wherein X is —N(CH$_3$)— and Y is —C(H)(OH). By administering the Compounds of the Invention, superior pharmacokinetic profile is achieved (e.g., longer residency time of the active compound in the body, particularly in the brain) relative to when the the active Compound of Formula Q is administered.

Wherein X is —N(CH$_3$)—, the Compounds of the Invention may further be metabolized in vivo to form the des-methyl derivative (i.e., wherein X is —N(H)—. In particular, the Compound of Formula I, wherein X is —N(CH$_3$) and Y is —C(H)(OH)— or —C(=O), may be metabolized to form the des-methyl derivative (e.g., wherein X is —N(H)— and Y is —C(H)(OH) or —C(=O)— respectively), wherein the hydroxy compound may then be oxidized in vivo to form the respective active desmethyl Compound of Formula Q, wherein X —N(H)— and Y is —C(=O).

In addition to the unique characteristic of the Compounds of the Invention, the Compounds of Formula I, wherein Y is —C(H)(OH)— may also be esterified to form physiologically hydrolysable and acceptable ester prodrugs. As used herein, "physiologically hydrolysable and acceptable esters" means esters of Compounds of the Invention which are hydrolysable under physiological conditions to yield hydroxy on the one hand and acid, e.g., carboxylic acid on the other, which are themselves physiologically tolerable at doses to be administered. For Example, the Compound of Formula I wherein Y is —C(H)(OH) may be esterified to form a prodrug, i.e., a Compound of Formula III or any of formulae 4.1-4.27 or 4.28-4.30. For example, the Compound of Formula I wherein Y is —C(H)(OH)— or any of 1.1-1.17 or 1.19-1.22, may be esterified to form a Compound of Formula III, which may be hydrolyzed in vivo to form the Compound of Formula I, wherein Y is —C(H)(OH)— and then oxidized in vivo to the respective active Compound of Formula Q. In particular, the Compound of Formula III, wherein R$_1$ is —C(O)—C$_{1-21}$alkyl, e.g., acyl acid esters, e.g., heptanoic, octanoic, decanoic, dodecanoic, tetradecanoic or hexadecanoic acid ester may be hydrolyzed in the body to form the Compound of Formula I wherein Y is —C(H)(OH)— on the one hand and HO— C(O)—C$_{1-21}$alkyl on the other (e.g., heptanoic, octanoic, decanoic, dodecanoic, tetradecanoic or hexadecanoic acid respectively), which hydroxy compound will then be converted to the active Compound of Formula Q wherein Y is —C(=O)—.

Similarly, wherein the Compounds of the Invention contain an amine group, prodrug of such amine, e.g., methyl amine prodrugs may also exist wherein the prodrug is cleaved to release the amine metabolite in vivo following administration.

The prodrugs of the Compounds of the Invention, i.e., the Compounds of Formula III, particularly when R$_1$ is —C(O)—C$_{1-21}$alkyl, preferably —C$_{6-21}$alkyl, more preferably C$_{6-15}$alkyl, more preferably linear, saturated or unsaturated and optionally substituted with one or more hydroxy or alkoxy groups, is particularly useful for sustained- and/or delayed release so as to achieve a long acting effect, e.g., wherein the Compounds of the Invention is released over a period of from about 14 to about 30 to about 180 days, preferably over about 30 or about 60 or about 90 days, for example as described in any of depot composition of any of formulae 5.5-5.9 or 5.10-5.11. Preferably, the sustained and/or delayed-release formulation is an injectable formulation.

Alternatively and/or additionally, the Compounds of the Invention (e.g., Compounds of Formula I or any of 1.1-1.22, Formula II-A, Formula II-B, or Formula III or any of formulae 4.1-4.27 or 4.28-4.30) may be included as a depot formulation, e.g., by dispersing, dissolving or encapsulating the Compounds of the Invention in a polymeric matrix as described in any of composition 6.1-6.4 or 6.5, such that the Compound is continually released as the polymer degrades over time. The release of the Compounds of the Invention from the polymeric matrix provides for the controlled- and/or delayed- and/or sustained-release of the Compounds, e.g., from the pharmaceutical depot composition, into a subject, for example a warm-blooded animal such as man, to which the pharmaceutical depot is administered. Thus, the pharmaceutical depot delivers the Compounds of the Invention to the subject at concentrations effective for treatment of the particular disease or medical condition over a sustained period of time, e.g., 14-180 days, preferably about 30, about 60 or about 90 days.

Polymers useful for the polymeric matrix in the Composition of the Invention (e.g., Depot composition of the Invention) may include a polyester of a hydroxyfatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethyleneglycol copolymer or polyglycolic acid-polyethyleneglycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly (lactic acid), or PLA). Most preferably, the polymer is the biodegradable poly(d,l-lactide-co-glycolide) polymer.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly(glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl(polylactide-co-glycolide). It is preferred that the molar ratio of lactide to glycolide in such a copolymer be in the range of from about 75:25 to 50:50.

Useful PLGA polymers may have a weight-average molecular weight of from about 5,000 to 500,000 daltons, preferably about 150,000 daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerisation with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

In another embodiment, the polymeric matrix useful for the invention may comprise a star polymer wherein the structure of the polyester is star-shaped. These polyesters have a single polyol residue as a central moiety surrounded by acid residue chains. The polyol moiety may be, e.g., glucose or, e.g., mannitol. These esters are known and described in GB 2,145, 422 and in U.S. Pat. No. 5,538,739, the contents of which are incorporated by reference.

The star polymers may be prepared using polyhydroxy compounds, e.g., polyol, e.g., glucose or mannitol as the initiator. The polyol contains at least 3 hydroxy groups and has a molecular weight of up to about 20,000 Daltons, with at least 1, preferably at least 2, e.g., as a mean 3 of the hydroxy groups of the polyol being in the form of ester groups, which contain polylactide or co-polylactide chains. The branched polyesters, e.g., poly (d,l-lactide-co-glycolide) have a central glucose moiety having rays of linear polylactide chains.

The depot composition of the invention (e.g., compositions of any of formulae 6.1-6.4 or 6.5) as hereinbefore described may comprise the polymer in the form of microparticles or nanoparticles, or in a liquid form, with the Compounds of the Invention dispersed or encapsulated therein. "Microparticles" is meant solid particles that contain the Compounds of the Invention either in solution or in solid form wherein such compound is dispersed or dissolved within the polymer that serves as the matrix of the particle. By an appropriate selection of polymeric materials, a microparticle formulation can be made in which the resulting microparticles exhibit both diffusional release and biodegradation release properties.

When the polymer is in the form of microparticles, the microparticles may be prepared using any appropriate method, such as by a solvent evaporation or solvent extraction method. For example, in the solvent evaporation method, the Compounds of the Invention and the polymer may be dissolved in a volatile organic solvent (for example a ketone such as acetone, a halogenated hydrocarbon such as chloroform or methylene chloride, a halogenated aromatic hydrocarbon, a cyclic ether such as dioxane, an ester such as ethyl acetate, a nitrile such as acetonitrile, or an alcohol such as ethanol) and dispersed in an aqueous phase containing a suitable emulsion stabiliser (for example polyvinyl alcohol, PVA). The organic solvent is then evaporated to provide microparticles with the Compounds of the Invention encapsulated therein. In the solvent extraction method, the Compounds of the Invention and polymer may be dissolved in a polar solvent (such as acetonitrile, dichloromethane, methanol, ethyl acetate or methyl formate) and then dispersed in an aqueous phase (such as a water/PVA solution). An emulsion is produced to provide microparticles with the Compounds of the Invention encapsulated therein. Spray drying is an alternative manufacturing technique for preparing the microparticles.

Another method for preparing the microparticles of the invention is also described in both U.S. Pat. No. 4,389,330 and U.S. Pat. No. 4,530,840.

The microparticle of the present invention can be prepared by any method capable of producing microparticles in a size range acceptable for use in an injectable composition. One preferred method of preparation is that described in U.S. Pat. No. 4,389,330. In this method the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle product can be blended in the solvent medium together.

Solvents for the Compounds of the Invention and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as, benzyl alcohol; ethyl acetate; and the like. In one embodiment, the solvent for use in the practice of the present invention may be a mixture of benzyl alcohol and ethyl acetate. Further information for the preparation of microparticles useful for the invention can be found in U.S. Patent Publication Number 2008/0069885, the contents of which are incorporated herein by reference in their entirety.

The amount of the Compounds of the Invention incorporated in the microparticles usually ranges from about 1 wt % to about 90 wt. %, preferably 30 to 50 wt. %, more preferably 35 to 40 wt. %. By weight % is meant parts of the Compounds of the Invention per total weight of microparticle.

The pharmaceutical depot may comprise a pharmaceutically-acceptable diluent or carrier, such as a water miscible diluent or carrier.

Details of Osmotic-controlled Release Oral delivery System composition may be found in EP 1 539 115 (U.S. Pub. No. 2009/0202631) and WO 2000/35419, the contents of each of which are incorporated by reference in their entirety.

A "therapeutically effective amount" is any amount of the Compounds of the invention (for example as contained in the pharmaceutical depot) which, when administered to a subject suffering from a disease or disorder, is effective to cause a reduction, remission, or regression of the disease or disorder over the period of time as intended for the treatment.

Dosages employed in practicing the present invention will of course vary depending, e.g. on the particular disease or condition to be treated, the particular Compound of the Invention used, the mode of administration, and the therapy desired. Unless otherwise indicated, an amount of the Compound of the Invention for administration (whether administered as a free base or as a salt form) refers to or is based on the amount of the Compound of the Invention in free base form (i.e., the calculation of the amount is based on the free base amount).

Compounds of the Invention may be administered by any satisfactory route, including orally, parenterally (intravenously, intramuscular or subcutaneous) or transdermally, but are preferably administered orally. In certain embodiment, the Compounds of the Invention, e.g., in depot formulation, is preferably administered parenterally, e.g., by injection.

In general, satisfactory results for Method I or any of formulae 7.1-7.25 or Method Ip or use of the Compounds of the Invention as hereinbefore described, e.g. for the treatment of a combination of diseases such as a combination of at least depression, psychosis, e.g., (1) psychosis, e.g., schizophrenia, in a patient suffering from depression; (2) depression in a patient suffering from psychosis, e.g., schizophrenia; (3) mood disorders associated with psychosis, e.g., schizophrenia, or Parkinson's disease; and (4) sleep disorders associated with psychosis, e.g., schizophrenia, or Parkinson's disease, as set forth above are indicated to be obtained on oral administration at dosages of the order from about 1 mg to 100 mg once daily, preferably 2.5 mg-50 mg, e.g., 2.5 mg, 5 mg, 10 mg, 20 mg, 30 mg, 40 mg or 50 mg, once daily, preferably via oral administration.

Satisfactory results for Method II or any of 8.1-8.15, Method $II_P$ or use of the Compounds of the Invention as hereinbefore described, e.g. for the treatment of sleep disorder alone are indicated to be obtained on oral administration at dosages of the order from about 2.5 mg-5 mg, e.g., 2.5 mg, 3 mg, 4 mg or 5 mg, of a Compound of the Invention, in free or pharmaceutically acceptable salt form, once daily, preferably via oral administration.

Satisfactory results for Method I-A or any of 9.1-9.38 or Method $I_P$-A are indicated to be obtained at less than 100 mg, preferably less than 50 mg, e.g., less than 40 mg, less than 30 mg, less than 20 mg, less than 10 mg, less than 5 mg, less than 2.5 mg, once daily. Satisfactory results for Method II-A or any of 9.1-9.38 are indicated to be obtained at less than 5 mg, preferably less than 2.5 mg.

For treatment of the disorders disclosed herein wherein the depot composition is used to achieve longer duration of action, the dosages will be higher relative to the shorter action composition, e.g., higher than 1-100 mg, e.g., 25 mg, 50 mg, 100 mg, 500 mg, 1,000 mg, or greater than 1000 mg. Duration of action of the Compounds of the Invention may be controlled by manipulation of the polymer composition, i.e., the polymer:drug ratio and microparticle size. Wherein the composition of the invention is a depot composition, administration by injection is preferred.

The pharmaceutically acceptable salts of the Compounds of the Invention can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, nonaqueous media like ether, ethyl acetate, ethanol, isopropanol, or acetonitrile are preferred. Further details for the preparation of these salts, e.g., toluenesulfonic salt in amorphous or crystal form, may be found in PCT/US08/03340 and/or U.S. Provisional Appl. No. 61/036,069.

Pharmaceutical compositions comprising Compounds of the Invention may be prepared using conventional diluents or excipients (an example include, but is not limited to sesame oil) and techniques known in the galenic art. Thus oral dosage forms may include tablets, capsules, solutions, suspensions and the like.

Methods of Making the Compounds of the Invention:

The Compounds of the Invention wherein Y is —C(H)(OH)— may be prepared by reacting a reducing agent with the Compound of Formula Q, wherein Y is —C(=O) as hereinbefore described, which starting compound of Formula Q may be prepared as described in further details in WO PCT/US08/03340 (WO 2008/112280); U.S. application Ser. No. 10/786,935; U.S. Pat. Nos. 6,548,493; 7,238,690; 6,552,017; 6,713,471; 7,183,282; U.S. RE39680, and U.S. RE39679, the contents of which are incorporated by reference in their entirety. The reducing agent may be a metal hydride, e.g., sodium borohydride, sodium cyanoborohydride, lithium aluminum hydride, aluminum hydride, diisobutylaluminium hydride, preferably sodium borohydride. Further reagents for reduction of ketones may be found in Jerry March, Advanced Organic Chemistry, Reactions Mechanisms and Structures, p. 910-911, (1992, John Wiley & Sons, Inc.), Fourth Edition, the contents of which are incorporated by reference.

Wherein X is —N(H)— and Y is —C(H)(OH), the compounds of the Invention (e.g., Formula I) is alternatively prepared by reacting the Compound of Formula I wherein X is —N(CH₃)— and Y is —C(H)(OH)— with the reducing agents as described above for the reduction of the ketone group of Formula Q, for example, by using sodium borohydride.

Isolation or purification of the disastereomers of the Compounds of the Invention may be achieved by conventional methods known in the art, e.g., column purification, preparative thin layer chromatography, preparative HPLC, crystallization, trituration, simulated moving beds and the like.

The Compounds or of Formula III or any of 4.1-4.27 or 4.28-4.30may be prepared by several commonly used esterification methods such as alcoholysis of acyl halides, anhydrides or active esters. For example, The Compound of Formula III, wherein $R_1$ is —C(O)-alkyl may be prepared by reacting:

(a) L-C(O)—$C_{1-21}$alkyl, wherein L is a leaving group such as a halo group (for example, chloro or bromo), trifluoromethylsulfonyloxy (—OS(O)$_2$CH$_3$), tosyloxy (—O—S(O)$_2$—C$_6$H$_4$—CH$_3$), methylsulfonyloxy (—O—S(O)$_2$—CH$_3$), 1H-benzo[d][1,2,3]triazol-1-yloxy or succinimidyloxy group, with (b) the Compound of Formula I wherein Y is —C(H)(OH), preferably in the presence of a base (e.g., diisopropylamine, triethyl amine or pyridine). For example L-C(O)—$C_{1-21}$alkyl is an acetyl halide, decanoyl halide or heptanoyl halide, which may be prepared by reacting HO—C(O)—$C_{1-21}$alkyl, e.g., with thionyl chloride, P(X')$_3$ or P(X')$_5$ wherein X' is Cl or Br. Wherein L is tosyloxy-C(O)—$C_{1-21}$alkyl or methylsulfonyloxy-C(O)—$C_{1-21}$alkyl, these compounds may be prepared by reacting HO—C(O)—$C_{1-21}$alkyl with tosyl-chloride or mesyl-chloride, preferably in the presence of a base such as pyridine. Synthesis of the Compound of Formula II may be summarized in the reaction scheme below:

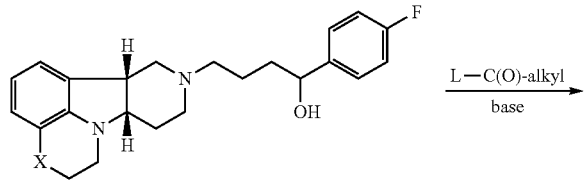

Formula I wherein
Y is —C(H)(OH) and
X as hereinbefore described

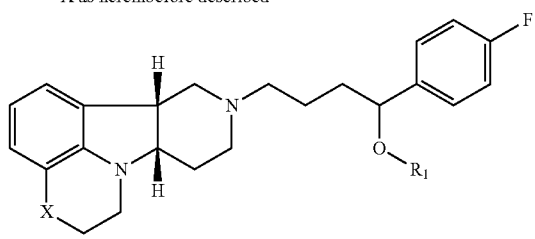

Formula III as hereinbefore described

Alternatively, the synthesis of the compound of Formula III maybe achieved by reacting HO—C(O)—$C_{1-21}$alkyl with (i) a compound of Formula I wherein Y is —C(H)(OH) in the presence of a base such as DIEPA and NEt$_3$, and (ii) a dehydrating or coupling reagent such as 2-fluoro-1-ethyl pyridinium tetrafuoroborate (FEP), tetramethylfuoromamidinium hexafuorophosphate (TFFH) or 1,1,3,3-bis (tetramethylene) chlorouronium hexafluorophosphate (PyClU).

Salts of the Compounds of the Invention may be prepared as similarly described in U.S. Pat. Nos. 6,548,493; 7,238,690; 6,552,017; 6,713,471; 7,183,282; U.S. RE39680; U.S. RE39679; and WO 2009/114181, the contents of each of which are incorporated by reference in their entirety.

Example 1

Synthesis of 1-(4-Fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-ol

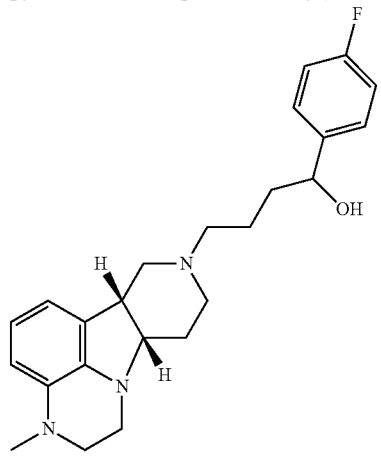 [SMILES: CN1CCN2c3c(cccc31)[C@@H]1CN(CCCC(O)c3ccc(F)cc3)CC[C@@H]12]

1-(4-Fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one tosylate salt (8.58 g, 15.2 mmol) is dissolved in 150 mL of methanol. The obtained brown solution is cooled to −10° C., and then NaBH$_4$ (1.72 g, 45.5 mmol) is added slowly. After the addition is complete, the reaction mixture is stirred at room temperature for an hour, and then quenched by adding 20 mL of water. After solvent is removed by rotary evaporation, the residue is treated with 50 mL of 1N NaOH aqueous solution, and then extracted with methylene chloride four times. The combined organic phase is washed with water, dried with anhydrous sodium sulfate, and then evaporated to dryness under vacuum to give 6 g of white foamy solids with 97.8% purity and 99% yield. MS (ESI) m/z 396.1 [M+H]+.

Diastereomers of this compound are separated by HPLC using CHIRALPAK® AY-H, 5µ, 30×250 mm at room temperature and eluted with 10% ethanol/90% hexane/0.1% dimethylethylamine. Peaks are detected at 230 nm to produce 98-99.9% ee of the diastereomer.

Example 2

Synthesis of 1-(4-Fluoro-phenyl)-4-((6bR,10aS)-2,3,6b,9,10,10a-hexahydro-1H,7H-pyrido[3',4':4,5]pyrrolo[1,2,3-de]quinoxalin-8-yl)-butan-1-ol

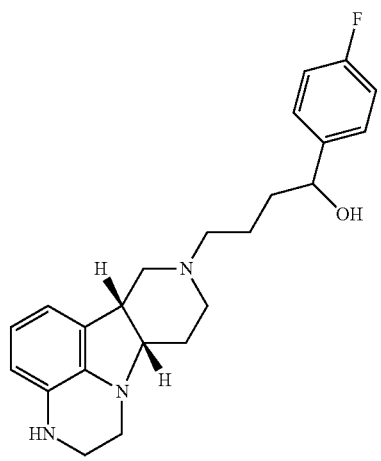 [SMILES: OC(CCCN1CC[C@H]2[C@@H](C1)c1cccc3c1N2CCN3)c1ccc(F)cc1]

1-(4-Fluoro-phenyl)-4-((6bR,10aS)-2,3,6b,9,10,10a-hexahydro-1H,7H-pyrido[3',4':4,5]pyrrolo[1,2,3-de]quinoxalin-8-yl)-butan-1-one HCl salt (500 mg, 1.20 mmol) is suspended in 20 mL of methanol. NaBH$_4$ (136 mg, 3.60 mmol) is added slowly into the suspension at room temperature. The suspension changed into a clear solution during the addition of NaBH$_4$. After an hour, additional 90 mg of NaBH$_4$ is added into the mixture to push the reaction to completion. The reaction mixture is quenched by adding 10 mL of water. After solvent is removed by rotary evaporation, the residue is treated with 10 mL of 1N NaOH aqueous solution, and then extracted with methylene chloride three times. The combined organic phase is washed with water, dried with anhydrous sodium sulfate, and then evaporated to dryness under vacuum to give 434 mg off-white foamy solids with 98% purity and 95% yield. MS (ESI) m/z 382.2 [M+1-1]+

Example 3

Synthesis of 1-(4-Fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-decanoate

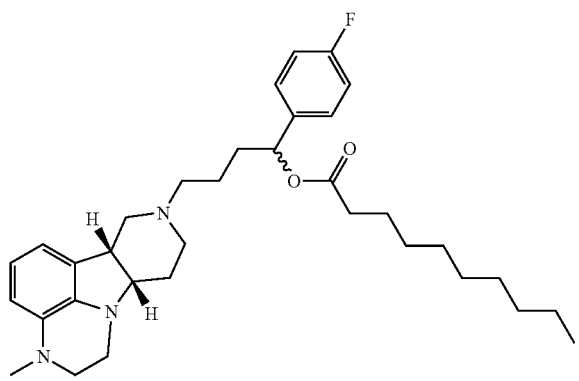 [SMILES: CCCCCCCCCC(=O)OC(CCCN1CC[C@H]2[C@@H](C1)c1cccc3c1N2CCN3C)c1ccc(F)cc1]

One hundred and seventy-two mg of decanoic acid (1.0 equivalent) is dissolved in 1.0 ml dichloromethane (DCM) at room temperature, and oxalyl chloride (1.0 equivalent) is dropped in followed by 2 drops of N,N-dimethyfomamide (DMF). The clear solution is stirred for 1.0 h to prepare decanoic acid chloride, which is used directly for the next step.

Three hundred and ninety-six mg of 1-(4-Fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-ol (1.0 equiv.) as similarly prepared in Example 1, and 1.5 equiv. of N,N-dimethyl-4-aminopyridine (DMAP) are dissolved in 3.0 ml DCM under stiffing. The freshly prepared decanoic acid chloride solution is dropped in slowly at room temperature, and the mixture is stirred for additional 2.0 h until thin layer chromatograph (TLC) indicates all starting material is consumed. Upon completion of reaction, two milliliters of water is dropped in to quench the reaction and the pH is adjusted to >9 with 30% NaOH. The organic layer is separated and concentrated. The crude product is purified by column chromatography (ethylacetate:methanol=5:1) to yield 160 mg decanoic ester free base as brown oil. R$_t$ (UPLC-MS)=3.42 min, HRMS for C$_{34}$H$_{48}$FN$_3$O$_2$ (M$^+$+1) 550.1024.

Example 4

Synthesis of 1-(4-Fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-butanoate

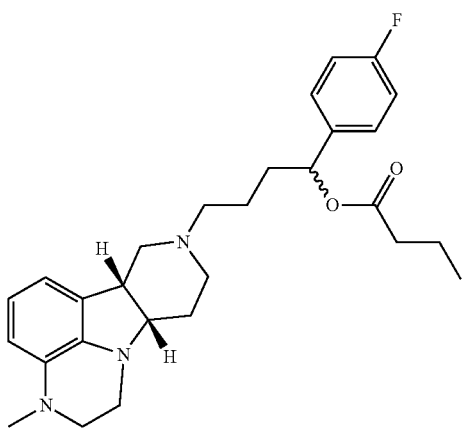 [SMILES: CCCC(=O)OC(CCCN1CC[C@H]2[C@@H](C1)c1cccc3c1N2CCN3C)c1ccc(F)cc1]

This compound is synthesized using similar procedure as described in Example 3 to yield free base of 1-(4-Fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-butanoate as brown oil. R$_t$ (UPLC-MS)=2.54 min, HRMS for C$_{28}$H$_{36}$FN$_3$O$_2$ (M$^+$+1) 466.0489.

Example 5

Single Dose Oral Bioavailability and Pharmacokinetic Study in Sprague Dawley Rats Animals are Used for the Study:
 Strain/Species: Sprague Dawley (Crl:CD®(SD)BR) Rat
 Sex: Male and Female
 Age at Receipt: 7-8 weeks
 Weight Range: 225-300 g
 Number of Animals on Study: 3 Males and 3 Females
Preparation of Dosage Formulation
 The suspension of 1-(4-Fluoro-phenyl)-4-((6bR,10aS)-3-methyl-2,3,6b,9,10,10a-hexahydro-1H,7H-pyrido-[3',4':4,5]pyrrolo[1,2,3-de]quinoxalin-8-yl)-butan-1-ol (i.e., Compound of Example 1) is prepared using deionized water containing 0.5% methylcellulose. The suspension is prepared by placing the required amount of methylcellulose in deionized water in a glass container. The suspension are kept stirring with a magnetic stirrer until completion of daily dosing. The dose suspensions are prepared on the day of dosing for each test article group.
 A total of 3 male and 3 female rats are dosed at 30 mg/kg. Blood samples are collected at 0.30 min, 1, 4 and 8 h after dosing. Plasma samples are analyzed to determine plasma concentrations of the Compound of Example 1, the Compound of Formula Q wherein X is —N(CH$_3$)— and Y is —C(=O), and the Compound of Formula Q wherein X is —N(H)— and Y is —C(=O). The pharmacokinetic profile is determined using WinNonlin
 Animals are anesthetized with isoflurane, and whole blood (~0.5 mL/time point) is collected from the orbital sinus utilizing a glass capillary tube on the first day of treatment at the following times: 0.30 min, 1, 4 and 8 h after dosing. Whole blood (~0.5 mL) is collected into chilled plastic tubes containing sodium heparin as supplied by the manufacturer. The blood collection tubes are mixed several times by manual inversion or gentle vortexing and stored on wet ice until centrifugation. The blood is centrifuged (~2700 g, ~10 min, ~5° C.). Plasma is transferred with disposable plastic pipettes to plastic vials and stored at approximately −70° C. until analyzed. The results are summarized in Table 2:

TABLE 2

| Gender | Parameter | Example 1 | | Formula Q, wherein X is —N(H)— and Y is C(=O) | | Formula Q, wherein X is —N(CH$_3$)— and Y is C(=O) | |
|---|---|---|---|---|---|---|---|
| | | Mean | SD | Mean | SD | Mean | SD |
| Male | t$_{max}$ (h) | 0.83 | 0.29 | 1 | 0 | 0.75 | 0.35 |
| | C$_{max}$ (ng/mL) | 91.63 | 63.46 | 5.84 | 5.52 | 4.85 | 5.31 |
| | AUC$_{last}$ (ng·h/mL) | 421.38 | 373.72 | 37.42 | 42.03 | 54.53 | — |
| | t$_{1/2}$ (h) | 5.83 | 1.04 | 17.77 | 12.61 | 12.09 | — |
| Female | t$_{max}$ (h) | 3.33 | 4.04 | 5.33 | 2.31 | 1 | 0 |
| | C$_{max}$ (ng/mL) | 144.37 | 119.62 | 12.78 | 10.64 | 11.76 | 4.16 |
| | AUC$_{last}$ (ng·h/mL) | 766.82 | 652.95 | 89.73 | 75.20 | 71.01 | 28.44 |
| | t$_{1/2}$ (h) | 11.58 | 3.04 | — | — | 23.37 | 11.06 |

As observed in Table 2, the concentration of the Compound of Example 1 in the plasma generally decreases over time while the concentration of the Compound of Formula Q wherein X is —N(CH$_3$)— and Y is —C(=O) or X is —N(H)— and Y is —C(=O)— is maintained over 8 hours.

Example 6

SERT Activity

Inhibition of serotonin reuptake transport (SERT) activity and binding to SERT by 1-(4-Fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-ol is measured using imipramine as a reference, using the methods described in WO/2009/145900. The compound is found to have potent SERT inhibitory activity, similar to the corresponding keto compound of Formula Q.

Inhibition of serotonin uptake is measured in a human platelet assay, using tritiated serotonin. The platelets are diluted in Ca-free KRH buffer containing 0.5 mM EDTA, pH 7.4, and added to control and test samples for 15 minutes at room temperature. Tubes are then equilibrated in a 37° C. water bath before addition of substrate. Reaction is stopped by rapid vacuum filtration after a 15 minute incubation. Radioactivity trapped onto the filters is determined and compared to control values in order to ascertain any interactions of test compound with serotonin uptake. The K$_T$ (binding affinity of tritiated serotonin) in this assay is 970 nM. The V$_{max}$ (transport rate) is 25 pmol/min/mg protein. The test compound has a Ki of 1.5 micromolar. The positive control, imipramine, has a K$_i$ of 0.1 micromolar in this assay.

Inhibition of binding to SERT is measured using tritiated citalopram as competitor. The receptor source in this assay is human platelet membranes. The radioligand is [$^3$H] Citalopram, N-Methyl (70-87 Ci/mmol). The final ligand concentration is [0.7 nM]. Clomipramine—[1.0 μM] is a nonspecific determinant and the positive control in imipramine. Reactions are carried out in 50 mM TRIS-HCl (pH 7.4), containing 120 mM NaCl and 5 mM KCl at 25° C. for 60 minutes. The reaction is terminated by rapid vacuum filtration onto glass fiber filters. Radioactivity trapped onto the filters is determined using liquid scintillation spectrometry and compared to control values in order to ascertain any interactions of test compound with the serotonin transporter binding site. The K$_D$ (binding affinity of citalopram) in this assay is 2.5 nM and the B$_{max}$ (receptor number) is 425 fmol/mg protein. The test compound has a K$_i$ of 71 nM, compared to a K$_i$ of 3 nM for the imipramine positive control.

Example 7

Hydrolysis of Example 4 in Whole Rate Blood

The hydrolysis rate of 1-(4-Fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-butanoate (or the compound of Example 4) in EDTA-containing rat whole blood is measured by incubation of the sample with whole rat blood at 37 degrees temperature for various times, taking samples at every five-minute intervals, the remaining concentration of starting drug is and the hydrolyzed ester are measured by HPLC-MS after extraction of the blood with acetonitrile. The results are shown in Table 3 below:

TABLE 3

| | Concentration/μM | | | | | | |
|---|---|---|---|---|---|---|---|
| | 0 min | 5 min | 10 min | 15 min | 30 min | 60 min | 90 min |
| Example 4 | 52.84 | 24.92 | 18.51 | 9.21 | 7.06 | 2.74 | 1.75 |
| Example 1 | | 8.43 | 12.02 | 13.42 | 19.21 | 24.66 | 33.31 |

As can be seen from Table 3, the compound of Example 4 is steadily cleaved back to the compound of Example 1 with the evidence of increasing concentration of the compound of Example 1 in the blood during 90 minutes.

Example 8

DOI (DOI (R(−)-2,5-dimethoxy-4-iodoamphetamine))-induced head twitch test in mice DOI is an agonist of the serotonin 5-HT2 receptor family. When administered to mice, it produces a behavioral profile associated with frequent head twitches. The frequency of these head twitches during a predetermined period of time can be taken as an estimate of 5-HT2 receptor agonism in the brain. Conversely, this behavioral assay can be used to determine 5-HT2 receptor antagonism in the brain by administering the DOI with or without an antagonist and recording the reduction in DOI-induced head twitches after the administration of the antagonist.

The method of Darmani et al., *Pharmacol Biochem Behav.* (1990) 36:901-906 (the contents of which are incorporated by reference in their entirety) is used with some modifications. (±)-DOI HCl is injected subcutaneously and the mice are immediately placed in a conventional plastic cage. The number of head twitches is counted during 6 min, beginning 1 min after DOI administration. The compound of Example 1 is administered orally 0.5 hr before the injection of DOI. The results are shown in FIG. 1.

As can be seen in the FIG. 1, oral administration of the compound of Example 1 before DOI significantly and dose dependently reduced head twitches, indicative of activity as a 5-HT2 receptor antagonist. The IC50 of the compound of Example 1 for reducing DOI-induced head twitches in this assay is 0.31 mg/kg.

Example 9

Step-Down Latency Test

Drugs that antagonize dopamine receptors in the brain slow motor behavior and can induce a cataleptic state. This activity can be assessed in mice using a simple step down latency test. In this test, mice are held by the tail, and the rodents forepaws are placed on a rod and its hindpaws placed on the bench top. The time for forepaws to step down from the rod is then measured. A maximum of 2 min is allowed at which time the animal is taken away from the rod and returned to the home cage. The compound of Example 1 or haloperidol (used as a positive control) is administered orally 120 minutes before the first test. Step down latency tests are conducted at 120, 180, 240, and 360 minutes after the administration of the compound of Example 1 or haloperidol. After each test mice are returned to their cages. The results are show in FIG. 2.

Figure 2:
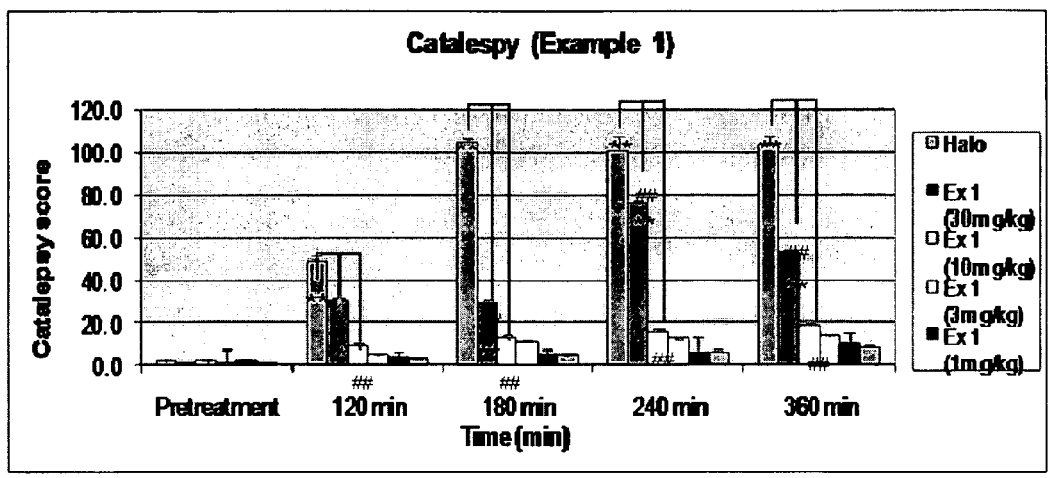
FIG. 2 illustrates the inhibition of step down latency in mice after oral administration of the compound of Example 1 as described in Example 9.

As can be seen in the FIG. 2, oral administration of the compound of Example 1 significantly and dose dependently increased step down latency, indicative of activity as a dopamine receptor antagonist.

The invention claimed is:

1. A compound of Formula I:

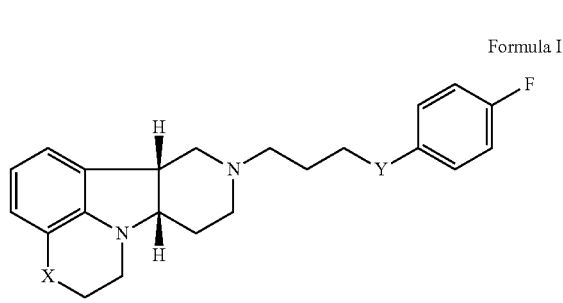

Formula I wherein:

X is —N(H)— or —N(CH$_3$)— and Y is —C(H)(OH)—;

in solid free base or salt form.

2. A compound of Formula I

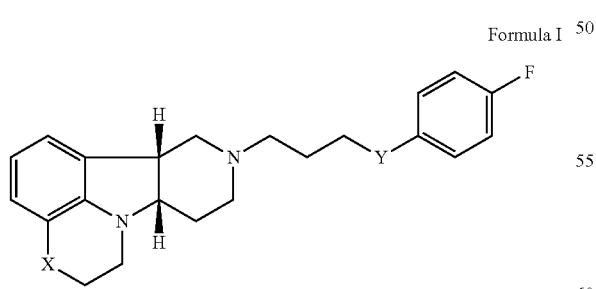

Formula I wherein:

X is —N(H)— or —N(CH$_3$)— and Y is —C(H)(OH)—;

in free base or pharmaceutically acceptable salt form, wherein said compound is greater than 70% free of a compound of Formula Q:

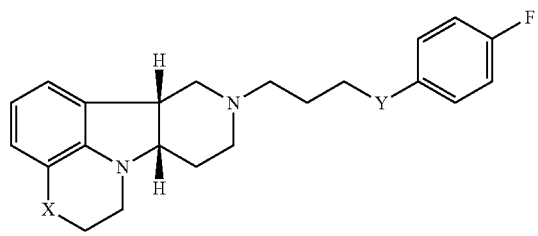

Formula Q wherein

X is —N(H)— or —N(CH$_3$)— and Y is —C(=O).

3. The compound according to claim 2, wherein said compound is greater than 90% free of the compound of Formula Q.

4. The compound according to claim 2, wherein X is —N(CH$_3$)—, in free base or pharmaceutically acceptable salt form.

5. A compound of Formula III:

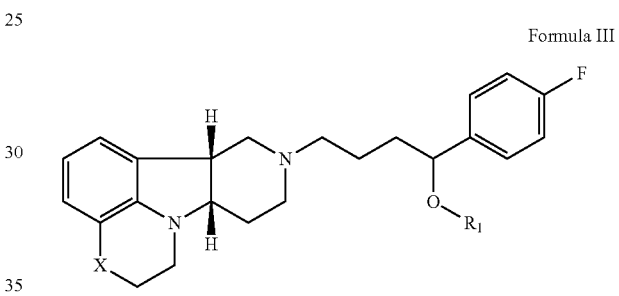

Formula III wherein:

X is —N(CH$_3$)— or —N(H)—; and

R$_1$ is —C(O)—C$_{1-21}$alkyl optionally saturated or unsaturated and optionally substituted with one or more hydroxy or C$_{1-22}$alkoxy groups, in free base or salt form.

6. The compound according to claim 5, wherein

R$_1$ is —C(O)—C$_3$alkyl, in free base or salt form.

7. The compound according to claim 6, wherein the compound of Formula III is:

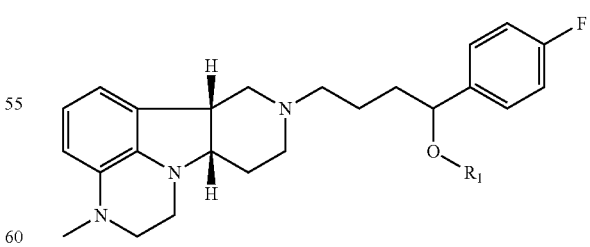

in free base or salt form.

8. The compound according to claim 5, wherein X is —N(CH$_3$)—, in free base or salt form.

9. The compound according to claim 5, wherein said compound is selected from the group consisting of:

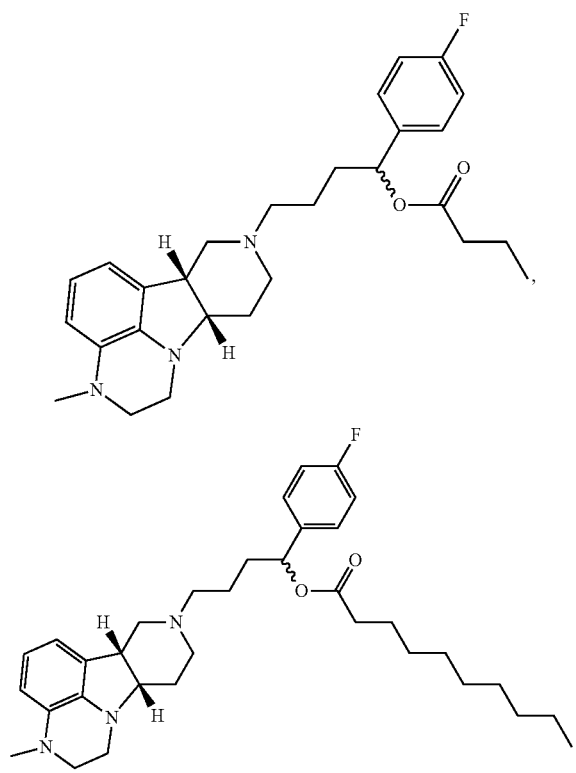

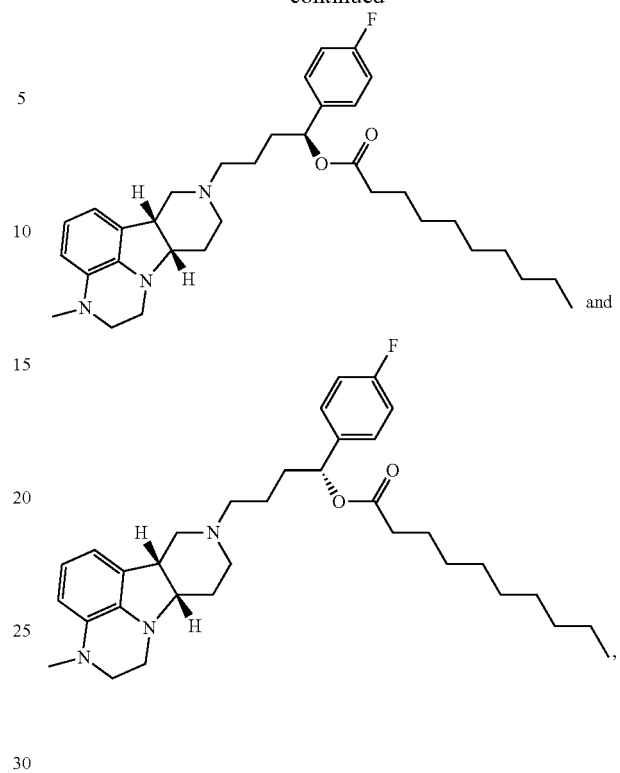

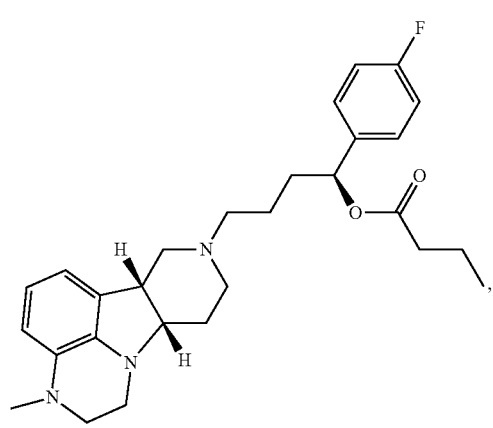

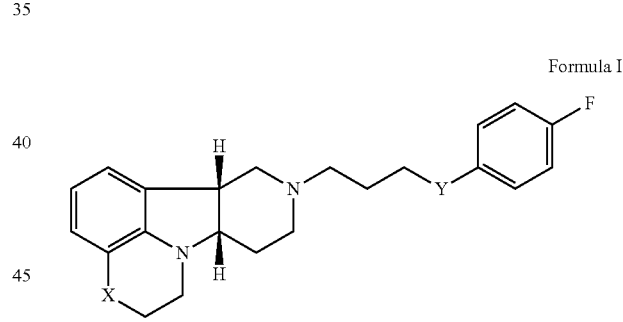

and

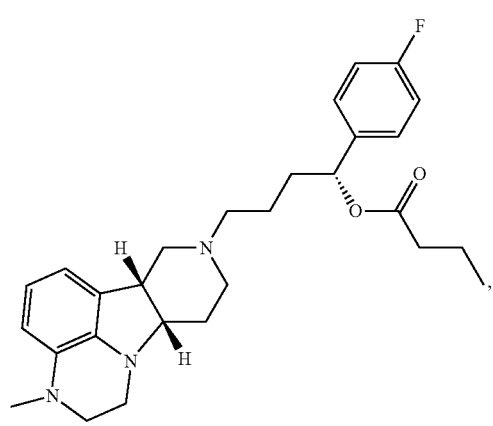

in free base or salt form.

10. A pharmaceutical composition comprising a compound of formula I:

Formula I wherein:

X is —N(H)— or N(CH$_3$)— and Y is —C(H)(OH)—;

in free base or pharmaceutically acceptable salt form, in admixture with a pharmaceutically acceptable diluent or carrier.

11. The pharmaceutical composition according to claim 10, wherein said compound is in a pharmaceutically acceptable salt form.

12. The pharmaceutical composition according to claim 11, wherein the pharmaceutically acceptable salt is selected from a group consisting of toluenesulfonic, fumaric and phosphoric acid addition salts.

13. The pharmaceutical composition according to claim 10, wherein said compound is:

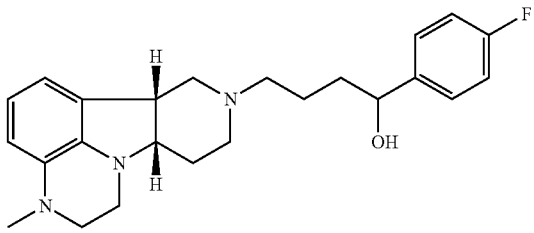 [SMILES: CN1CCN2c3c(cccc31)[C@@H]1CN(CCCC(O)c3ccc(F)cc3)CC[C@@H]12]

in free base or pharmaceutically acceptable salt form.

14. The pharmaceutical composition according to claim 13, wherein said compound is in free base form.

15. The pharmaceutical composition according to claim 10, wherein the compound of formula I is in free base form.

16. A pharmaceutical composition comprising a compound of Formula II-A:

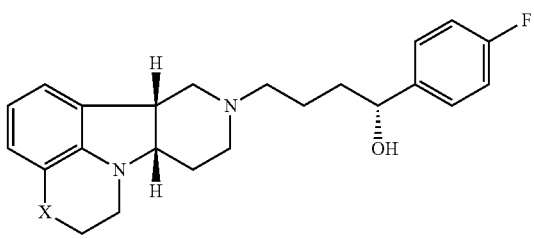

wherein X is —N(CH$_3$)— or —N(H)—, in free base or pharmaceutically acceptable salt form, in admixture with a pharmaceutically acceptable diluent or carrier.

17. The pharmaceutical composition according to claim 16, wherein X is —N(CH$_3$)—, in free base or pharmaceutically acceptable salt form.

18. A pharmaceutical composition comprising a compound of Formula II-B:

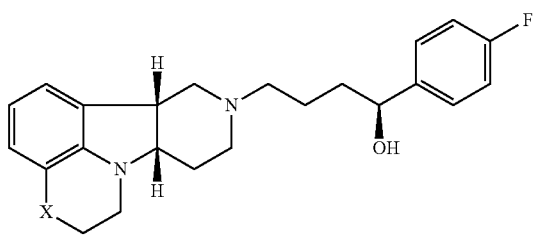

wherein X is —N(CH$_3$)— or —N(H)—, in free base or pharmaceutically acceptable salt form, in admixture with a pharmaceutically acceptable diluent or carrier.

19. The pharmaceutical composition according to claim 18, wherein

X is —N(CH$_3$)—, in free base or pharmaceutically acceptable salt form.

* * * * *